United States Patent [19]

Arakawa et al.

[11] Patent Number: 5,028,784
[45] Date of Patent: Jul. 2, 1991

[54] METHOD FOR GENERATING RADIATION IMAGE SIGNALS, IMAGE PROCESSING METHOD, AND RADIATION IMAGE READ-OUT APPARATUS

[75] Inventors: Satoshi Arakawa; Wataru Ito; Kazuo Shimura; Toshitaka Agano, all of Kanagawa, Japan

[73] Assignee: Fuji Photo Film Co., Ltd., Kanagawa, Japan

[21] Appl. No.: 507,287

[22] Filed: Apr. 10, 1990

[30] Foreign Application Priority Data

| Apr. 11, 1989 | [JP] | Japan | 1-91240 |
| Jun. 9, 1989 | [JP] | Japan | 1-147536 |
| Jun. 9, 1989 | [JP] | Japan | 1-147537 |
| Jan. 24, 1990 | [JP] | Japan | 2-13910 |

[51] Int. Cl.$^5$ .................................. G01N 23/04
[52] U.S. Cl. .................... 250/327.2; 250/484.1; 382/10
[58] Field of Search ............... 250/327.2 G, 484.1 B; 382/41, 43, 54, 31, 10

[56] References Cited

U.S. PATENT DOCUMENTS

| 4,258,264 | 3/1981 | Kotera et al. |
| 4,276,473 | 6/1981 | Kato et al. |
| 4,282,511 | 8/1981 | Southgate et al. ............. 250/550 |
| 4,315,318 | 2/1982 | Kato et al. |
| 4,387,428 | 6/1983 | Ishida et al. |
| 4,674,045 | 6/1987 | Kerber et al. ............. 382/42 |

FOREIGN PATENT DOCUMENTS

| 0174659 | 3/1986 | European Pat. Off. |
| 0195563 | 9/1986 | European Pat. Off. |
| 56-11395 | 2/1981 | Japan |
| 61-5193 | 2/1986 | Japan |

OTHER PUBLICATIONS

Pratt, W., Digital Image Processing (1978), pp. 93-97, John Wiley & Sons.

*Primary Examiner*—Jack I. Berman
*Assistant Examiner*—Richard Hanig
*Attorney, Agent, or Firm*—Sughrue, Mion, Zinn, Macpeak & Seas

[57] ABSTRACT

A method for generating a radiation image signal comprises the steps of detecting an image signal by reading out a radiation image, which has been recorded on a recording medium during an image recording operation using a grid and which comprises an object image and a striped grid image corresponding to the grid and superposed upon the object image. The image signal is sampled such that a plurality of image signal components are obtained which correspond to a plurality of discrete points on the radiation image, intervals between the discrete points varying irregularly from predetermined intervals at least along a direction intersecting the striped pattern of the grid image on the radiation image.

35 Claims, 14 Drawing Sheets

F I G. 3
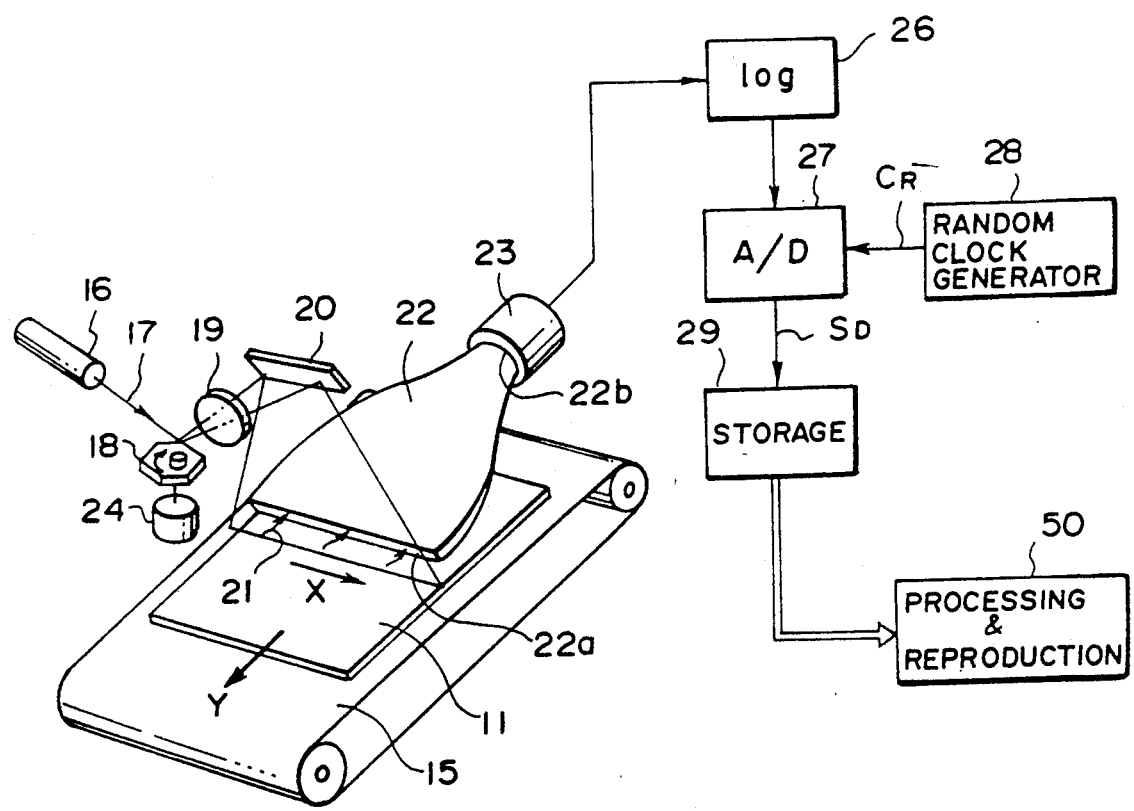

F I G.12
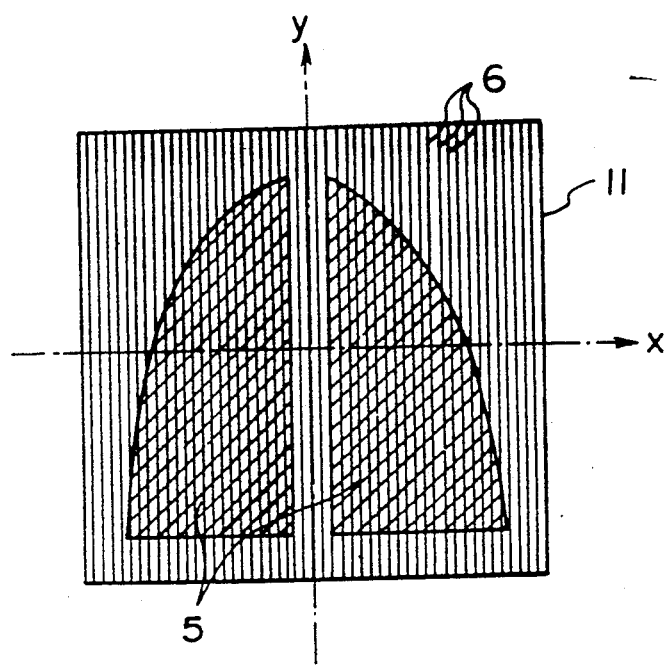

METHOD FOR GENERATING RADIATION IMAGE SIGNALS, IMAGE PROCESSING METHOD, AND RADIATION IMAGE READ-OUT APPARATUS

BACKGROUND OF THE INVENTION

1. Field of the Invention

This invention relates to a method for generating a radiation image signal wherein an image signal is obtained by reading out a radiation image which has been recorded on a recording medium during an image recording operation using a grid and which comprises an object image and a striped grid image corresponding to the grid and superposed upon the object image. This invention also relates to an image processing method for such a radiation image. This invention further relates to a radiation image read-out apparatus wherein a method for generating a radiation image signal is employed.

2. Description of the Prior Art

Techniques for reading out a recorded radiation image in order to obtain an image signal, carrying out appropriate image processing on the image signal, and then reproducing a visible image by use of the processed image signal have heretofore been known in various fields. For example, as disclosed in Japanese Patent Publication No. 61(1986)-5193, an X-ray image is recorded on a sheet of X-ray film having a small gamma value designed for the type of image processing to be carried out, the X-ray image is read out from the X-ray film and converted into an electric signal, and the electric signal (image signal) is processed and then used for reproducing the X-ray image as a visible image on a copy photograph or the like. In this manner, a visible image having good image quality with high contrast, high sharpness, high graininess, or the like can be reproduced.

Also, when certain kinds of phosphors are exposed to radiation such as X-rays, $\alpha$-rays, $\beta$-rays, $\gamma$-rays, cathode rays or ultraviolet rays, they store part of the energy of the radiation. Then, when the phosphor which has been exposed to the radiation is exposed to stimulating rays such as visible light, light is emitted by the phosphor in proportion to the amount of energy stored during exposure to the radiation. A phosphor exhibiting such properties is referred to as a stimulable phosphor. As disclosed in U.S. Pat. Nos. 4,258,264, 4,276,473, 4,315,318, 4,387,428, and Japanese Unexamined Patent Publication No. 56(1981)-11395, it has been proposed to use stimulable phosphors in radiation image recording and reproducing systems. Specifically, a sheet provided with a layer of the stimulable phosphor (hereinafter referred to as a stimulable phosphor sheet) is first exposed to radiation which has passed through an object such as the human body in order to store a radiation image of the object thereon, and is then scanned with stimulating rays, such as a laser beam, which cause it to emit light in proportion to the amount of energy stored during exposure to the radiation. The light emitted by the stimulable phosphor sheet, upon stimulation thereof, is photoelectrically detected and converted into an electric image signal. The image signal is then used to reproduce the radiation image of the object as a visible image on a recording material such as photographic film, a display device such as a cathode ray tube (CRT), or the like.

Radiation image recording and reproducing systems which use stimulable phosphor sheets are advantageous over conventional radiography using silver halide photographic materials, in that images can be recorded even when the energy intensity of the radiation to which the stimulable phosphor sheet is exposed varies over a wide range. More specifically, since the amount of light emitted upon stimulation after the radiation energy is stored on the stimulable phosphor varies over a wide range and is proportional to the amount of energy stored during exposure to the radiation, it is possible to obtain an image having a desirable density regardless of the energy intensity of the radiation to which the stimulable phosphor sheet was exposed. In order to obtain a desirable image density, an appropriate read-out gain is set when the emitted light is being detected and converted into an electric signal to be used in the reproduction of a visible image on a recording material or a display device.

During the recording of a radiation image of an object on a recording medium, such as X-ray film or a stimulable phosphor sheet, a grid is often located between the object and the recording medium such that radiation scattered by the object does not impinge upon the recording medium. The grid is constituted of bars of a radiation-impermeable material, such as lead, and bars of a radiation-permeable material, such as aluminium or wood, which are alternately located in parallel at small pitches of approximately 4.0 bars/mm. When the grid is used during the recording of a radiation image of an object on a recording medium, radiation scattered by the object is prevented from impinging upon the recording medium, and therefore the contrast of the radiation image of the object can be kept high. However, a grid image having a striped pattern is recorded together with the object image on the recording medium.

In general, in radiation image read-out apparatuses, wherein an image signal is detected from a recording medium which has a radiation image recorded thereon, light which is emitted from the recording medium and which carries information about the radiation image is photoelectrically detected and converted into an image signal. The image signal is then sampled at sampling intervals of $\Delta x = 1/(2.fss)$ corresponding to the spatial frequency, which is the maximum of a spatial frequency range necessary for image information. The spatial frequency, which is the maximum of a spatial frequency range necessary for image information, is herein denoted by fss. The sampled image signal is then digitized. In cases where the radiation image comprises the object image and a grid image superposed upon the object image, the image signal obtained in the manner described above includes not only the information representing the radiation image of the object but also noise which is caused to occur by the grid image. The noise will occur even if the spatial frequency of the grid image is higher than the maximum spatial frequency fss necessary for image information.

FIG. 6A is a graph showing the spatial frequency characteristics of a radiation image, which has been recorded on a recording medium and which comprises an object image and a grid image superposed upon the object image, along a direction intersecting perpendicularly to the striped pattern of the grid image.

By way of example, it is herein assumed that, during the recording of the radiation image, a grid having the bars of a radiation-impermeable material and the bars of a radiation-permeable material, which are alternately located in parallel at pitches of 4.0 bars/mm, was used. The spatial frequency of the grid image is 4 cycles/mm.

Also, it is assumed herein that the spatial frequency fss, which is the maximum of a spatial frequency range necessary for the reproduction of a visible radiation image of the object, is 2.5 cycles/mm.

FIG. 6B is an explanatory graph showing how noise occurs when an image signal is sampled at sampling intervals of $\Delta x = 1/(2 \cdot fss) = 0.2$ (mm) corresponding to the spatial frequency fss=2.5 (cycles/mm), i.e. is sampled five times per mm. When such sampling intervals are applied, it is possible to obtain information in the spatial frequency region which is below the spatial frequency fss=2.5 (cycles/mm), which is the maximum of a spatial frequency range necessary for the reproduction of a visible radiation image of the object.

In FIG. 6B, the same curve as that shown in FIG. 6A is indicated by the solid line. As indicated by the broken line, noise occurs at the position corresponding to 1 cycle/mm, with which the position of the peak occurring at 4 cycles/mm coincides when the curve indicated by the solid line is folded back from the part corresponding to fss=2.5 (cycles/mm). Such noise is referred to as aliasing. Specifically, the aliasing corresponding to a spatial frequency of 4 cycles/mm of the grid image occurs at the position corresponding to 1 cycle/mm.

FIG. 6C is a graph showing the spatial frequency characteristics of the radiation image represented by an image signal obtained from the sampling in which sampling intervals of $\Delta x = 1/(2 \cdot fss) = 0.2$ (mm) are applied.

In cases where a visible image is reproduced to a scale of one to one from the image signal, which includes the noise corresponding to the grid image and occurring at the position of 1 cycle/mm, a striped pattern having a spatial frequency of 1 cycle/mm occurs on the reproduced visible image. Even if the spatial frequency of the grid image falls within such a spatial frequency range that the grid image is not very perceptible, when an image signal is sampled, noise which constitutes a striped pattern will occur in such a spatial frequency range that the grid image is perceptible. When the sampled image signal is used in the reproduction of a visible image, a visible image having bad image quality is obtained.

SUMMARY OF THE INVENTION

The primary object of the present invention is to provide a method for generating a radiation image signal, which includes little noise due to a grid, from a radiation image which has been recorded on a recording medium during an image recording operation using the grid.

Another object of the present invention is to provide an image processing method wherein noise due to a grid is reduced or eliminated from an image signal detected from a radiation image which has been recorded on a recording medium during an image recording operation using the grid.

The specific object of the present invention is to provide a radiation image read-out apparatus wherein a method for generating a radiation image signal is employed.

The present invention provides a first method for generating a radiation image signal, which comprises the steps of:
i) detecting an image signal by reading out a radiation image which has been recorded on a recording medium during an image recording operation using a grid and which comprises an object image and a striped grid image corresponding to the grid and superposed upon the object image, and
ii) sampling said image signal such that a plurality of image signal components are obtained which correspond to a plurality of discrete points on said radiation image, intervals between said discrete points varying irregularly from predetermined intervals at least along a direction intersecting the striped pattern of said grid image on said radiation image.

The first method for generating a radiation image signal in accordance with the present invention is based on the findings that the aliasing occurs at a position corresponding to a specific spatial frequency (for example, 1 cycle/mm in FIG. 6B) because of the sampling intervals of $\Delta x$ being constant and adversely affects the image quality of a reproduced visible image.

With the first method for generating a radiation image signal in accordance with the present invention, an image signal is sampled such that a plurality of image signal components are obtained which correspond to a plurality of discrete points on the radiation image, intervals between the discrete points varying irregularly from predetermined intervals at least along a direction intersecting the striped pattern of the grid image on the radiation image. Therefore, aliasing does not occur at a position corresponding to a specific spatial frequency, and an image signal can be generated which includes little striped pattern due to the grid and which represents a radiation image having good image quality.

By way of example, random numbers may be used in order to vary the intervals between the discrete points irregularly. However, the variation in the intervals between the discrete points need not necessarily be completely irregular. For example, a certain pattern of the irregular variation in the intervals between the discrete points may be repeated with a substantially long period.

The present invention also provides a first image processing method, which comprises the steps of:
i) carrying out Fourier transformation on an image signal detected by reading out an image which has been recorded on a recording medium during an image recording operation using a grid and which comprises an object image and a striped grid image corresponding to the grid and superposed upon the object image,
ii) reducing or eliminating the frequency information corresponding t the striped pattern of said grid image from the frequency information which is obtained from the Fourier transformation, and
iii) carrying out inverse Fourier transformation on the frequency information obtained from the reducing or eliminating operation.

The present invention further provides a second image processing method, which comprises the steps of:
i) carrying out spatial-domain filtering processing on an image signal detected by reading out an image which has been recorded on a recording medium during an image recording operation using a grid and which comprises an object image and a striped grid image corresponding to the grid and superposed upon the object image, said spatial-domain filtering processing being effected such that spatial frequency components corresponding to the striped pattern of said grid image are reduced or eliminated.

With the first image processing method in accordance with the present invention, Fourier transformation is carried out on an image signal detected by reading out an image which has been recorded on a recording medium during an image recording operation using a grid and which comprises an object image and a striped grid image corresponding to the grid and superposed upon the object image. The frequency information corresponding to the striped pattern of the grid image is then reduced or eliminated from the frequency information which is obtained from the Fourier transformation. Thereafter, inverse Fourier transformation is carried out on the frequency information obtained from the reducing or eliminating operation. Therefore, an image signal obtained from the inverse Fourier transformation includes little or no noise corresponding to the striped pattern of the grid image. Accordingly, a visible image, which has good image quality and includes little or no striped pattern, can be reproduced from the image signal obtained from the inverse Fourier transformation.

With the second image processing method in accordance with the present invention, the spatial-domain filtering processing is carried out on an image signal detected by reading out an image which has been recorded on a recording medium during an image recording operation using a grid and which comprises an object image and a striped grid image corresponding to the grid and superposed upon the object image. The spatial-domain filtering processing is effected such that spatial frequency components corresponding to the striped pattern of the grid image are reduced or eliminated. Therefore, as with the first image processing method in accordance with the present invention, it is possible to reproduce a reproduced visible image, which has good image quality and includes little or no striped pattern, from the image signal obtained from the spatial-domain filtering processing.

As described above, with the first and second image processing methods in accordance with the present invention, the spatial-domain filtering or frequency spatial filtering is carried out on the image signal in order to reduce or eliminate the information representing the striped pattern of the grid image. Therefore, no striped pattern (artifact) due to the grid occurs when signal compression processing, an image enlargement or reduction processing, or any of other processes is carried out after the filtering processing. Also, in cases where the filtering is carried out on the image signal components corresponding to positions located along two directions, or in cases where the direction along which the striped pattern extends and the pitch of the striped pattern are detected automatically and the filtering is carried out on the image signal components corresponding to positions located along a single direction that intersects perpendicularly to the striped pattern, the pitch and orientation of bars of the grid need no be taken into consideration during the recording of an image.

The present invention still further provides a second method for generating a radiation image signal, wherein an image signal is detected by reading out a radiation image at predetermined sampling intervals from a recording medium on which the radiation image has been recorded during an image recording operation using a grid, said radiation image comprising an object image and a striped grid image corresponding to the grid and superposed upon the object image, which striped grid image has spatial frequencies higher than a spatial frequency, which is the maximum of a desired spatial frequency range, the method for generating a radiation image signal comprising the steps of:

i) in the course of reading out said radiation image, obtaining an original image signal by applying sampling intervals smaller than such sampling intervals that a spatial frequency of aliasing caused to occur by said grid image coincides with said spatial frequency, which is the maximum of the desired spatial frequency range, along at least a direction intersecting the striped pattern of said grid image, ii) subjecting said original image signal to filtering processing for reducing or eliminating the spatial frequency components corresponding to said striped pattern or to said aliasing, and ii) generating an image signal by sampling the original image signal, which has been obtained from said filtering processing, at such sampling intervals that said spatial frequency, which is the maximum of the desired spatial frequency range, is set as a Nyquist frequency.

The present invention also provides a first radiation image read-out apparatus, wherein an image signal is detected by reading out a radiation image at predetermined sampling intervals from a recording medium on which the radiation image has been recorded during an image recording operation using a grid, said radiation image comprising an object image and a striped grid image corresponding to the grid and superposed upon the object image, which striped grid image has spatial frequencies higher than a spatial frequency, which is the maximum of a desired spatial frequency range, wherein the improvement comprises the provision of:

i) a read-out means with which said radiation image is read out and an original image signal is obtained by applying sampling intervals smaller than such sampling intervals that a spatial frequency of aliasing caused to occur by said grid image coincides with said spatial frequency, which is the maximum of the desired spatial frequency range, along at least a direction intersecting the striped pattern of said grid image, ii) a filtering means which carries out filtering processing on said original image signal for reducing or eliminating the spatial frequency components corresponding to said striped pattern or to said aliasing, and ii) a sampling means with which an image signal is generated by sampling the original image signal, which has been obtained from said filtering processing, at such sampling intervals that said spatial frequency, which is the maximum of the desired spatial frequency range, is set as a Nyquist frequency.

The present invention further provides a second radiation image read-out apparatus, wherein the first radiation image read-out apparatus in accordance with the present invention is modified such that a storage means is provided for storing information about several types of grids, the recorded images of which have different spatial frequencies, and information about several types of filtering processing methods for reducing or eliminating the spatial frequency components corresponding to said striped pattern or to said aliasing, said filtering processing methods corresponding to the respective types of grids, an input means is provided for entering the information about the type of a grid which is to be used or was used during the recording of said radiation image, and said filtering means reads the information about the filtering processing method, which corresponds to the type of the grid designated by said input means, from said storage means and carries out said filtering processing on said original image signal by using said filtering processing method read from said storage means.

The present invention still further provides a third radiation image read-out apparatus, wherein the first radiation image read-out apparatus in accordance with the present invention is modified such that a storage means is provided for storing information about several types of grids, the recorded images of which have different spatial frequencies, and information about several type of filtering processing methods for reducing or eliminating the spatial frequency components corresponding to said striped pattern or to said aliasing, said filtering processing methods corresponding to the respective types of grids, a judgment means is provided for determining, from said original image signal, the spatial frequency of the grid image recorded together with said object image or the spatial frequency of the aliasing caused to occur by said grid image, and said filtering means reads the information about the filtering processing method, which corresponds to the spatial frequency of said grid image or of said aliasing determined by said judgment means, from said storage means and carries out said filtering processing on said original image signal by using said filtering processing method read from said storage means It depends on the sampling intervals applied during the detection of the original image signal whether the original image signal includes the image signal components representing the grid image or includes the image signal components representing the aliasing caused to occur by the grid image. Therefore, in cases where the original image signal includes the image signal components representing the grid image, the term "reducing or eliminating the spatial frequency components corresponding to a striped pattern or to aliasing" as used herein means reducing or eliminating the spatial frequency components corresponding to the striped pattern of the grid image. In cases where the original image signal includes the image signal components representing the aliasing, the term "reducing or eliminating the spatial frequency components corresponding to a striped pattern or to aliasing" as used herein means reducing or eliminating the spatial frequency components corresponding to the aliasing.

In the second method for generating a radiation image signal and the first to third radiation image read-out apparatuses in accordance with the present invention, the original image signal is obtained by reading out the radiation image at sampling intervals smaller than such sampling intervals that a spatial frequency of aliasing caused to occur by the grid image coincides with the spatial frequency, which is the maximum of the desired spatial frequency range. Therefore, the original image signal include spatial frequency components corresponding to the grid image or the aliasing due to the grid image, which components are higher than the spatial frequency, which is the maximum of a desired spatial frequency range. With the second method for generating a radiation image signal and the first to third radiation image read-out apparatuses in accordance with the present invention, the original image signal is subjected t the filtering processing for reducing or eliminating the spatial frequency components corresponding to the striped pattern of the grid image or to the aliasing. Thereafter, an image signal is generated by resampling the original image signal, which has been obtained from the filtering processing, at the sampling intervals corresponding to the spatial frequency, which is the maximum of the desired spatial frequency range. Therefore, the image signal thus generated includes little or no noise corresponding to the striped pattern of the grid image. Accordingly, a visible image, which has good image quality and includes little or no striped pattern due to the grid, can be reproduced from the ultimately generated image signal.

As described above, with the second method for generating a radiation image signal and the first to third radiation image read-out apparatuses in accordance with the present invention, an image signal is generated by sampling the original image signal, which has been obtained from the filtering processing, at the sampling intervals corresponding to the spatial frequency $f_{ss}$. Therefore, the storage capacity for the ultimately generated image signal can be kept small. Also, in cases where the ultimately generated image signal is transmitted to an image processing and reproducing apparatus, or the like, the time required to transmit the image signal can be kept short.

Also, the second method for generating a radiation image signal and the first to third radiation image read-out apparatuses in accordance with the present invention have the effects that not only the noise caused to occur by the grid but also high-frequency quantum noise are reduced by the filtering processing.

In some radiation image recording and reproducing systems, several types of grids may be used. With the second radiation image read-out apparatus in accordance with the present invention, the storage means is provided for storing information about several types of grids, the recorded images of which have different spatial frequencies, and information about several types of filtering processing methods corresponding to the respective types of grids. Also, the input means is provided for entering the information about the type of a grid which is to be used or wa used during the recording of the radiation image. The filtering means reads the information about the filtering processing method, which corresponds to the type of the grid designated by the input means, from the storage means and carries out the filtering processing on the original image signal by using the filtering processing method read from the storage means. Therefore, even in the radiation image recording and reproducing systems wherein several types of grids are used, the filtering processing can be carried out which is suitable for each grid used during the recording of a radiation image. Accordingly, it is possible to reproduce a visible image which has good image quality and includes little or no striped pattern due to the grid.

With the third radiation image read-out apparatus in accordance with the present invention, the judgment means which determines the spatial frequency of the grid image or of the aliasing from the original image signal is provided in lieu of the input means of the second radiation image read-out apparatus in accordance with the present invention. Therefore, judgment can be made automatically to determine which type of filtering processing method is to be read from the storage means and used in the filtering processing. Accordingly, like the second radiation image read-out apparatus in accordance with the present invention, even when several types of grids are used, the filtering processing can be carried out which is suitable for each grid used during the recording of a radiation image. Also, with the third radiation image read-out apparatus in accordance with the present invention, information about the grid used during the recording of a radiation image need not be entered manually from an input means. Therefore, the third radiation image read-out apparatus in accordance with the present invention is easier to operate than is the second radiation image read-out apparatus in accordance with the present invention.

BRIEF DESCRIPTION OF THE DRAWINGS

FIG. 3 is a perspective view showing an example of a radiation image read-out apparatus wherein an embodiment of the first method for generating a radiation image signal in accordance with the present invention is employed, FIG. 12 is a schematic view showing a radiation image which has been stored on a stimulable phosphor sheet during an image recording operation using a grid and which comprises an object image and a striped grid image corresponding to the grid and superposed upon the object image.

DESCRIPTION OF THE PREFERRED EMBODIMENTS

The present invention will hereinbelow be described in further detail with reference to the accompanying drawings.

Figure 1:
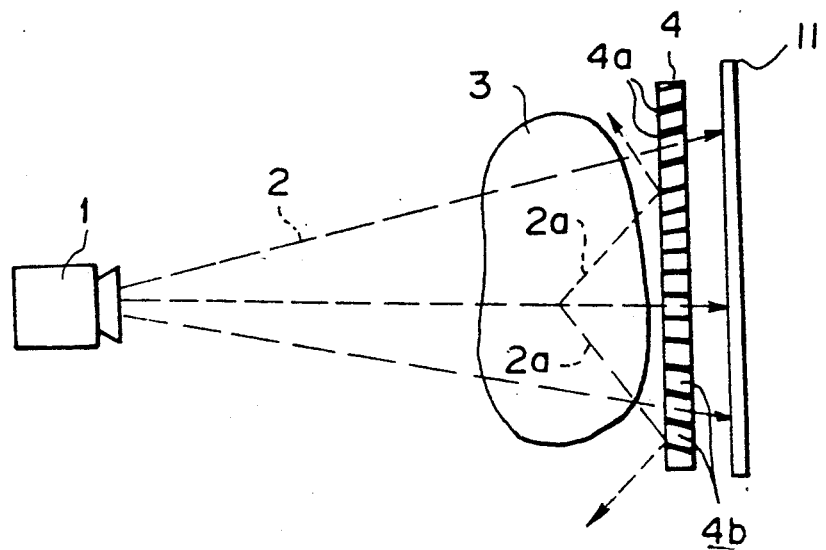
FIG. 1 is a schematic view showing an example of a radiation image recording apparatus.

FIG. 1 schematically shows an example of a radiation image recording apparatus. In the radiation image read-out apparatus, a stimulable phosphor sheet is used as a recording medium.

With reference to FIG. 1, radiation 2 is produced by a radiation source 1 and passes through an object 3. Thereafter, the radiation 2 passes through a grid 4 and impinges upon a stimulable phosphor sheet 11. The grid 4 is constituted of lead bars 4a, 4a, . . . and aluminium bars 4b, 4b, . . . which are alternately located in parallel at pitches of 4 bars/mm. The radiation 2 is blocked by the lead bars 4a, 4a, . . . and passes through the aluminium bars 4b, 4b, . . . . Therefore, an image of the object 3 and a striped grid image having a pattern of stripes at pitches of 4 stripes/mm are stored on the stimulable phosphor sheet 11. Radiation 2a scattered by the object 3 impinges obliquely upon the grid 4. Therefore, scattered radiation 2a is blocked or reflected by the grid 4 and does not impinge upon the stimulable phosphor sheet 11. Accordingly, a sharp radiation image free of adverse effects of the scattered radiation 2a is stored on the stimulable phosphor sheet 11.

Figure 2:
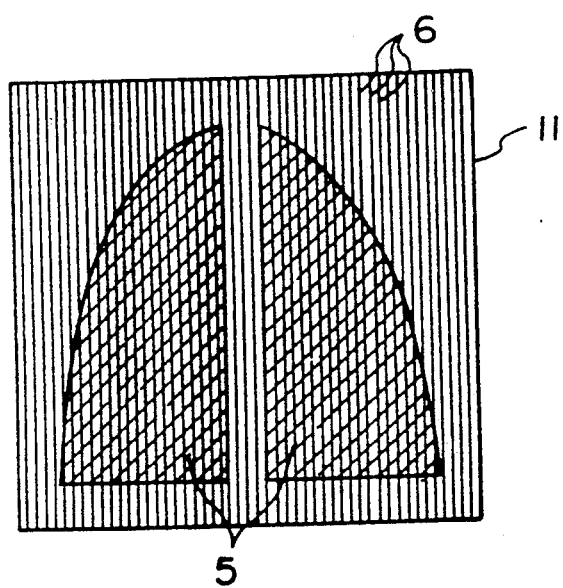
FIG. 2 is a schematic view showing a radiation image which has been stored on a stimulable phosphor sheet during an image recording operation using a grid and which comprises an object image and a striped grid image corresponding to the grid and superposed upon the object image.

FIG. 2 schematically shows a radiation image which has been stored on the stimulable phosphor sheet 11 during the image recording operation using the grid 4. The radiation image comprises an object image 5 (indicated by the oblique lines) and a striped grid image 6 (indicated by vertical stripes) which corresponds to the grid 4 and which is superposed upon the object image 5.

FIG. 3 is a perspective view showing an example of a radiation image read-out apparatus wherein an embodiment of the first method for generating a radiation image signal in accordance with the present invention is employed.

With reference to FIG. 3, the stimulable phosphor sheet 11, on which the radiation image has been stored, is placed at a predetermined position in the radiation image read-out apparatus. The stimulable phosphor sheet 11 is conveyed at a predetermined speed in a sub-scanning direction indicated by the arrow Y by a sheet conveyance means 15, which is constituted of an endless belt or the like and which is operated by an operating means (not shown). The stimulable phosphor sheet 11 has been placed at the predetermined position such that the striped pattern of the grid image 6 shown in FIG. 2 extends parallel to the sub scanning direction indicated by the arrow Y. A laser beam 17 produced by a laser beam source 16 is reflected and deflected by a rotating polygon mirror 18, which is quickly rotated by a motor 24 in the direction indicated by the arrow. Thereafter, the laser beam 17 passes through a converging lens 19 constituted of an fθ lens or the like. The direction of the optical path of the laser beam 17 is then changed by a mirror 20. The laser beam 17 impinges upon the stimulable phosphor sheet 11 and scans it at a predetermined speed Vx (mm/sec.) in a main scanning direction indicated by the arrow X. The main scanning direction is approximately normal to the subscanning direction indicated by the arrow Y. When the stimulable phosphor sheet 11 is exposed to the laser beam 17, the exposed portion of the stimulable phosphor sheet 11 emits light 21 in an amount proportional to the amount of energy stored thereon during its exposure to radiation. The emitted light 21 is guided by a light guide member 22, and photoelectrically detected by a photomultiplier 23. The light guide member 22 is made from a light guiding material such as an acrylic plate, and has a linear light input face 22a positioned so that it extends along the main scanning line on the stimulable phosphor sheet 11, and a ring-shaped light output face 22b positioned so that it is in close contact with a light receiving face of the photomultiplier 23. The emitted light 21, which has entered the light guide member 22 from its light input face 22a, is guided through repeated total reflection inside of the light guide member 22, emanates from the light output face 22b, and is received by the photomultiplier 23. In this manner, the amount of the emitted light 21 carrying the radiation image is converted into an electric signal by the photomultiplier 23.

An analog output signal S generated by the photomultiplier 23 includes signal components falling in the spatial frequency region above the spatial frequency $fss = 2.5$ (cycles/mm), which is the maximum of a desired spatial frequency range necessary for the reproduction of a visible radiation image having good image quality. Particularly, the analog output signal S includes the signal components, which represents the grid image 6 shown in FIG. 2 and which fall in the spatial frequency region above the spatial frequency fss. The signal components representing the grid image 6 adversely affect the image quality of a reproduced visible image and must be reduced or eliminated.

The analog output signal S is logarithmically amplified by a logarithmic amplifier 26. In an A/D converter 27, the amplified analog output signal S is sampled with the timing with which random clock pulses CR are generated by a random clock generator 28. The signal obtained from the sampling is digitized by the A/D converter 27 into a digital image signal SD. The digital image signal SD is stored in a storage means 29.

Figure 4A:
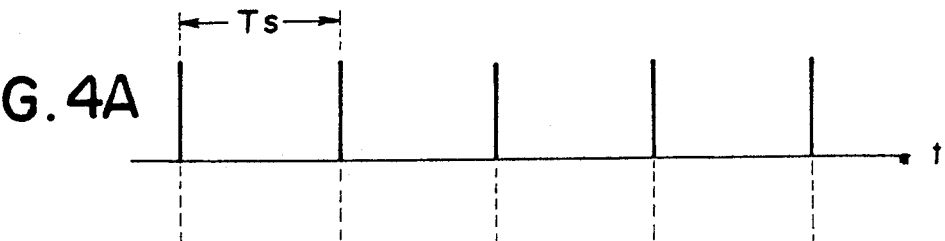
FIG. 4A is an explanatory graph showing a series of pulses generated at constant time intervals.
Figure 4B:
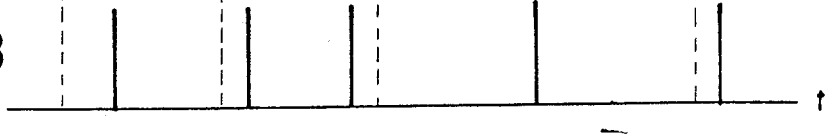
FIG. 4B is an explanatory graph showing random clock pulses generated by the random clock generator of the radiation image read-out apparatus shown in FIG. 3, FIGS. 5A and 5B are explanatory graphs showing another embodiment of the first method for generating a radiation image signal in accordance with the present invention.

FIG. 4A is an explanatory graph showing a series of pulses generated at constant time intervals of Ts. FIG. 4B is an explanatory graph showing the random clock pulses CR generated by the random clock generator 28 of the radiation image read-out apparatus shown in FIG. 3. In FIGS. 4A and 4B, the horizontal axis t represents the time base (sec.).

With reference to FIG. 4A, the time intervals of Ts correspond to the sampling intervals of $\Delta x = 1/(2 \cdot fss) = 0.2$ (mm). When the sampling intervals of 0.2 mm are applied, an image signal is obtained which represents the image information below the spatial frequency $fss = 2.5$ (cycles/mm), which is the maximum of a desired spatial frequency range necessary for the reproduction of a visible object image having good image quality from the stimulable phosphor sheet 11 shown in FIG. 3. The time intervals Ts are represented by the formula $$Ts = \frac{\Delta x}{Vx}$$

where Vx denotes the speed (mm/sec.) with which the laser beam 17 scans the stimulable phosphor sheet 11 in the main scanning direction.

With reference to FIG. 4B, the random clock pulses CR are generated with timing which varies at random with respect to the constant time intervals of Ts.

As described above, the random clock pulses CR are fed into the A/D converter 27 shown in FIG. 3. In the A/D converter 27, the amplified analog output signal S is sampled with the timing, with which the random clock pulses CR are generated by the random clock generator 28, and converted into the digital image signal SD.

The image signal SD is made up of image signal components sampled with the timing modulated at random. Therefore, aliasing due to the grid image 6 shown in FIG. 2 does not occur at a specific spatial frequency, and the image signal SD represents an image having good image quality.

In the embodiment described above, the stimulable phosphor sheet 11 is placed at the predetermined position in the radiation image read-out apparatus of FIG. 3 such that the striped pattern of the grid image 6 extends parallel to the sub-scanning direction indicated by the arrow Y in FIG. 3. In cases where the stimulable phosphor sheet 11 is placed at the predetermined position in the radiation image read-out apparatus of FIG. 3 such that the striped pattern of the grid image 6 extends parallel to the main scanning direction indicated by the arrow X, it is necessary that the sampling intervals along the sub-scanning direction be modulated at random. By way of example, the random modulation of the sampling intervals along the subscanning direction may be achieved by moving the mirror 20 at random or changing the speed, with which the stimulable phosphor sheet 11 is conveyed in the subscanning direction indicated by the arrow Y, at random, so that the intervals between main scanning lines vary randomly in the sub-scanning direction. In cases where the stimulable phosphor sheet 11 is placed at the predetermined position in the radiation image read-out apparatus of FIG. 3 such that the direction along which the striped pattern of the grid image 6 extends is not parallel to the main scanning direction nor to the subscanning direction or is unknown, it is necessary that both the sampling intervals along the main scanning direction and the sampling intervals along the subscanning direction be modulated at random.

The image signal SD generated in the manner described above is stored in the storage means 29 and is then fed therefrom into an image processing and reproducing apparatus 50. The image processing and reproducing apparatus 50 carries out the appropriate image processing on the image signal SD and reproduces a visible image from the processed image signal SD. Because the image signal SD fed into the image processing and reproducing apparatus 50 includes little or no adverse effects of the grid 4, a visible image having good image quality can be reproduced from the image signal SD.

Another embodiment of the first method for generating a radiation image signal in accordance with the present invention will be described hereinbelow with reference to FIGS. 5A and 5B.

Figure 5A:
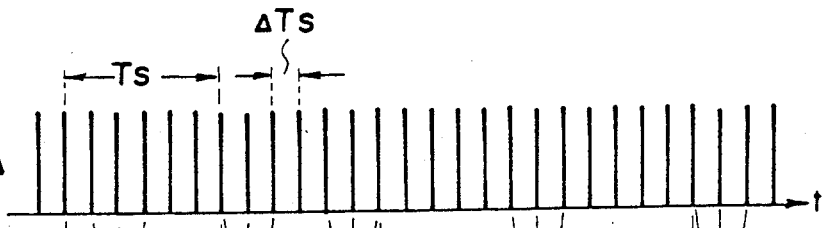
Figure 5B:
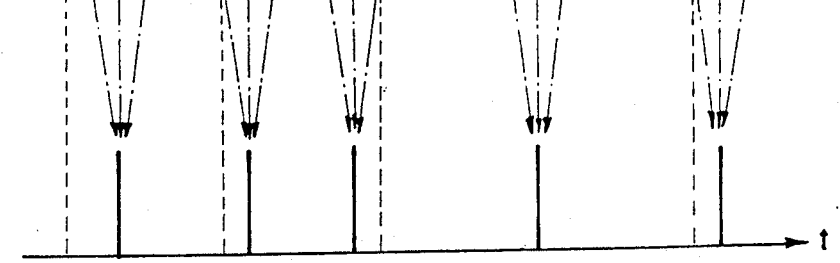
Figure 6A:
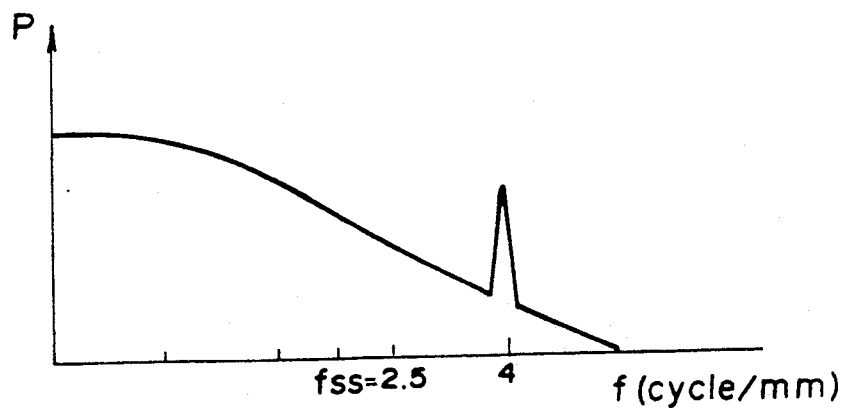
FIG. 6A is a graph showing the spatial frequency characteristics of a radiation image, which has been recorded on a recording medium and which comprises an object image and a grid image superposed upon the object image, along a direction intersecting perpendicularly to the striped pattern of the grid image.
Figure 6B:
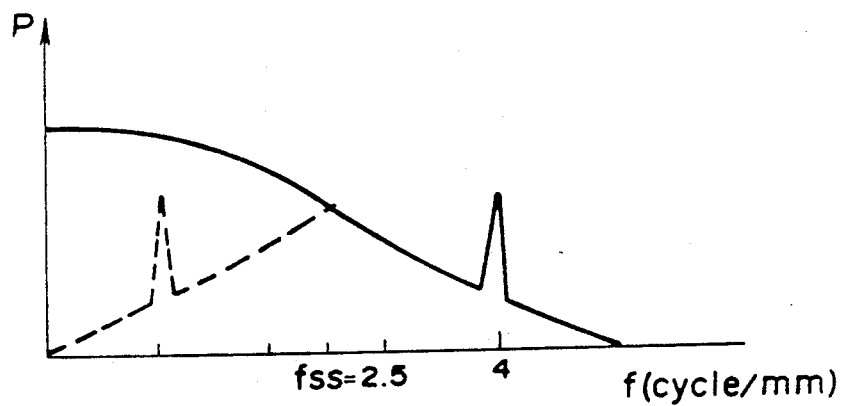
FIG. 6B is a graph showing the curve of FIG. 6A and aliasing which occurs in an image signal sampled at sampling intervals of $\Delta x = 1/(2 \times 2.5) = 0.2$ (mm) corresponding to a spatial frequency fss=2.5 (cycles/mm), which is the maximum of a desired spatial frequency range.
Figure 6C:
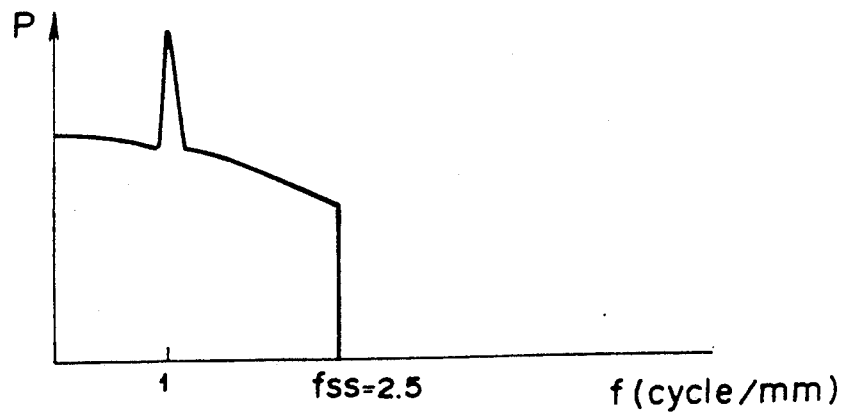
FIG. 6C is a graph showing the spatial frequency characteristics of a radiation image represented by an image signal sampled at sampling intervals of 0.2 mm, which are the same as in FIG. 6B.

FIG. 5A shows a series of pulses generated at constant time intervals of ΔTs which are markedly shorter than the sampling intervals of Ts necessary for the reproduction of a visible object image. The pulses shown in FIG. 5A are generated by a clock generator, which is employed in lieu of the random clock generator 28 shown in FIG. 3, and fed into the A/D converter 27. The A/D converter 27 samples a plurality of image signal components at time intervals of ΔTs from the amplified analog output signal S. Thereafter, as shown in FIG. 5B, an image signal is extracted with random timing from the image signal components.

As described above, constant sampling intervals (ΔTs) may be applied during the sampling from the amplified analog output signal S, and an image signal may be ultimately obtained which comprises image signal components corresponding to random sampling intervals. The image signal may be simply extracted from a plurality of image signal components obtained from the sampling at time intervals of ΔTs. Alternatively, as indicated by the chained lines in FIG. 5B, the mean values of the values of several neighboring image signal components may be calculated, and components having the mean values may be set as new image signal components corresponding to random sampling intervals. As for the sub-scanning direction, the small sampling intervals of ΔTs can be set by, for example, decreasing the speed with which the stimulable phosphor sheet 11 shown in FIG. 3 is conveyed.

In the aforesaid embodiments, stimulable phosphor sheets are used. However, the first method for generating a radiation image signal in accordance with the present invention is widely applicable when radiation images are read out, which have been recorded on recording media during image recording operations using grids and each of which comprises an object image and a striped grid image corresponding to the grid and superposed upon the object image. For example, the first method for generating a radiation image signal in accordance with the present invention is applicable also when X-ray image signals are detected from X-ray films having X-ray images recorded thereon.

Embodiments of the image processing method in accordance with the present invention will be described hereinbelow.

Figure 7:
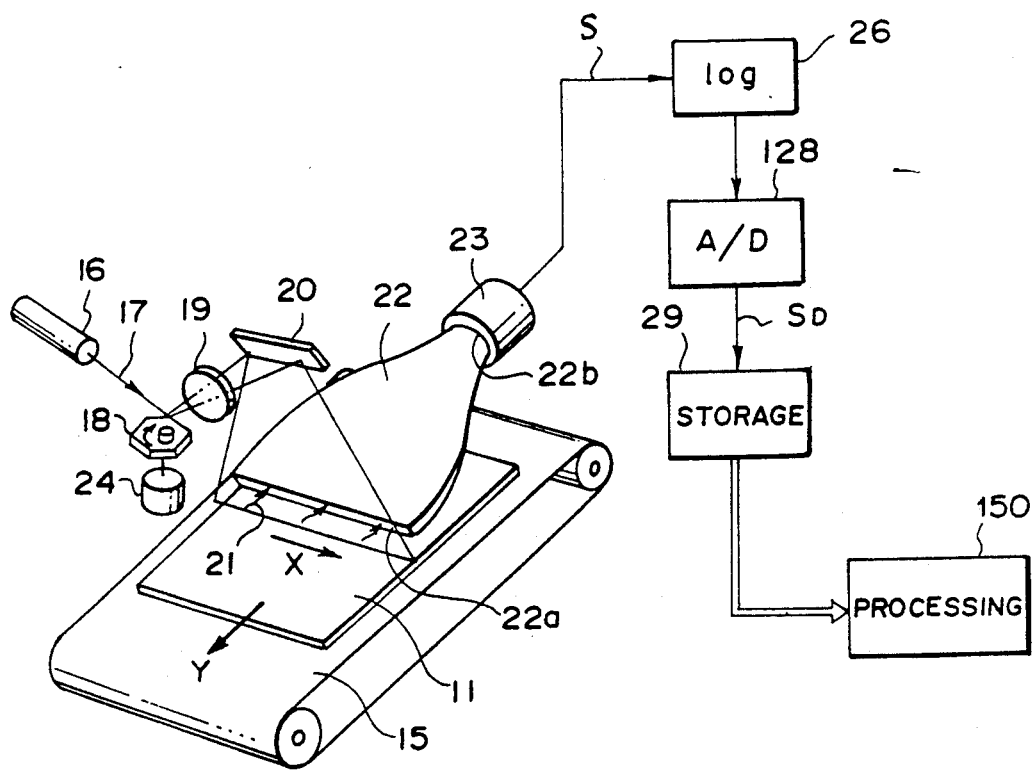
FIG. 7 is a perspective view showing an example of the radiation image read-out apparatus wherein an embodiment of the image processing method in accordance with the present invention is employed.

FIG. 7 is a perspective view showing an example of the radiation image read-out apparatus wherein an embodiment of the image processing method in accordance with the present invention is employed. In FIG. 7, similar elements are numbered with the same reference numerals with respect to FIG. 3.

With reference to FIG. 7, an analog output signal S is generated by the photomultiplier 23 during the image read-out operation carried out on the stimulable phosphor sheet 11 shown in FIG. 2, on which the radiation image comprising the object image 5 and the striped grid image 6 have been stored. The analog output signal S is logarithmically amplified by the logarithmic amplifier 26. The amplified analog output signal S is then sampled at predetermined sampling intervals and digitized by an A/D converter 128. In this manner, a digital image signal SD is obtained. The digital image signal SD is stored in the storage means 29 and thereafter fed into an image processing apparatus 150.

How the image processing apparatus 150 carried out image processing in order to reduce or eliminate noise due to the grid 4 shown in FIG. 1 will be described hereinbelow.

Figure 8:
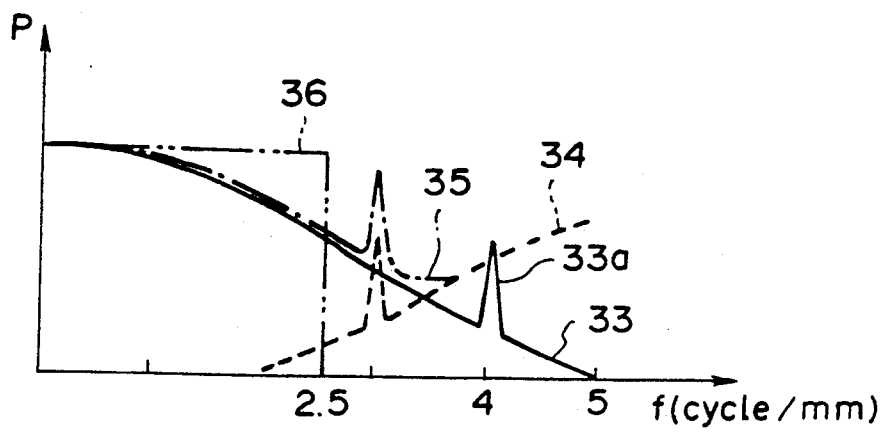
FIG. 8 is a graph showing the spatial frequency characteristics of a radiation image, which has been stored on a stimulable phosphor sheet and which comprises an object image and a grid image superposed upon the object image, along a direction intersecting perpendicularly to the striped pattern of the grid image, and the spatial frequency characteristics of a radiation image represented by an image signal sampled at sampling intervals of 0.14 mm along the direction intersecting perpendicularly to the striped pattern of the grid image.

FIG. 8 is an explanatory graph showing an embodiment of the image processing method in accordance with the present invention, which is carried out in the image processing apparatus 150.

With reference to FIG. 8, curve 33 indicated by the solid line represents the spatial frequency characteristics of the radiation image along a direction intersecting perpendicularly to the striped pattern of the grid image 6 shown in FIG. 2. The spatial frequencies of the radiation image range up to 5 cycles/mm, and a peak 33a is present at the position corresponding to 4 cycles/mm. Curve 34 indicated by the broken line illustrates aliasing occurring when the image signal is sampled at sampling intervals of 0.14 mm in the radiation image read-out apparatus shown in FIG. 7. Curve 35 indicated by the one-dotted chain line represents the spatial frequency characteristics of a radiation image represented by the image signal SD, which is obtained from the sampling at sampling intervals of 0.14 mm along the direction intersecting perpendicularly to the striped pattern of the grid image 6. Aliasing of the peak 33a corresponding to the striped pattern occurs at the position corresponding to a spatial frequency of approximately 3 cycles/mm.

The maximum of the spatial frequency range necessary for reproducing a visible image from the image signal SD is 2.5 cycles/mm. Therefore, Fourier transformation is carried out on the image signal SD. As indicated by the two-dotted chain line 36, the spatial frequency components below 2.5 cycles/mm are kept unremoved, and the spatial frequency components above 2.5 cycles/mm are removed. Thereafter, inverse Fourier transformation is carried out on the spatial frequency components below 2.5 cycles/mm. In this manner, spatial frequency components corresponding to the striped pattern due to the grid are eliminated, and only the necessary spatial frequency components are obtained.

Figure 9A:
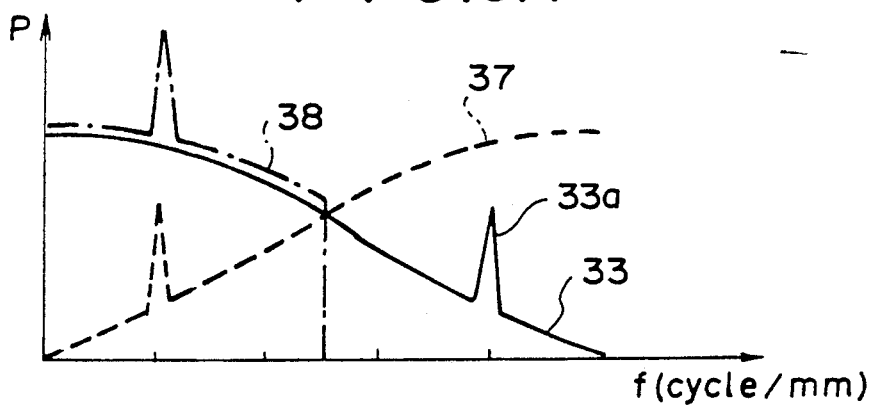
FIG. 9A is a graph showing the spatial frequency characteristics of a radiation image, which has been stored on a stimulable phosphor sheet and which comprises an object image and a grid image superposed upon the object image, along a direction intersecting perpendicularly to the striped pattern of the grid image, and the spatial frequency characteristics of a radiation image represented by an image signal sampled at sampling intervals of 0.2 mm along the direction intersecting perpendicularly to the striped pattern of the grid image.
Figure 9B:
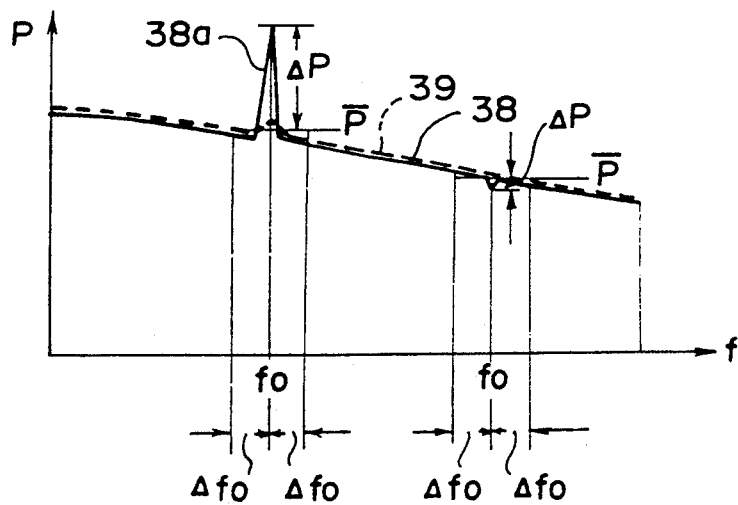
FIG. 9B is a horizontally enlarged graph showing the spatial frequency characteristics of a radiation image represented by an image signal which are shown in FIG. 9A.

FIGS. 9A and 9B are explanatory graphs showing another embodiment of the image processing method in accordance with the present invention.

With reference to FIG. 9A, curve 33 indicated by the solid line is the same as the curve 33 in FIG. 8 and represents the spatial frequency characteristics of the radiation image along a direction intersecting the striped pattern of the grid image 6 shown in FIG. 2. Curve 37 indicated by the broken line illustrates aliasing. Curve 38 indicated by the chained line represents the spatial frequency components of an image represented by an image signal SD. In this embodiment, the radiation image is read out at sampling intervals of 0.2 mm. Therefore, aliasing of the peak 33a occurs at the position corresponding to a spatial frequency of 1 cycle/mm.

As in the embodiment described with reference to FIG. 8, information having spatial frequencies up to 2.5 cycles/mm is necessary for the reproduction of a visible image having good image quality. Therefore, in this case, the same process as in the embodiment described with reference to FIG. 8 cannot be employed. In the embodiment of FIG. 9A, the process described below is carried out.

FIG. 9B is a horizontally enlarged graph showing the curve 38 illustrated in FIG. 9A (i.e. the spatial frequency characteristics of the radiation image represented by the image signal SD). The vertical axis of the graph indicates the intensity P of spatial frequency components.

With reference to FIG. 9B, Fourier transformation is carried out on the image signal, and the frequency information as illustrated is generated. Thereafter, a width of $\Delta fo$ is set on both sides of every spatial frequency fo. The mean value $\overline{P}$ of the intensities P of the spatial frequency components falling within the range of $fo - \Delta fo$ to $fo + \Delta fo$ is calculated. Thereafter, the difference, $P - \overline{P}$, between the intensity P and the mean value $\overline{P}$ corresponding to fo is compared with predetermined threshold values $Th1 = (1+\alpha) \cdot \overline{P}$ and $Th2 = (1-\alpha) \cdot \overline{P}$, where $\alpha$ is a positive number smaller than 1. In cases where P > Th1, or P < Th2, it is determined that a peak corresponding to the grid is present at the spatial frequency fo, and the intensity P corresponding to the spatial frequency fo is substituted by the mean value $\overline{P}$. In this manner, a peak 38a illustrated in FIG. 9B is eliminated as represented by curve 39 indicated by the broken line.

After the peak 38a is eliminated in the manner described above, an image signal including little or no adverse effects of the striped pattern can be obtained by carrying out inverse Fourier transformation.

In this embodiment of the image processing method in accordance with the present invention, the mean value $\overline{P}$ of the intensities P of the spatial frequency components falling within the range of $fo - \Delta fo$ to $fo + \Delta fo$ is utilized. Alternatively, a median value of the intensities P may be employed. Also, the threshold values need not necessarily be determined from the mean value $\overline{P}$ as in the cases of Th1 and Th2.

A further embodiment of the image processing method in accordance with the present invention will be described hereinbelow. In this embodiment, after Fourier transformation is carried out on the image signal, a histogram of the intensities P (frequency information) of the spatial frequency components falling within the range of $fo - \Delta fo$ to $fo + \Delta fo$ around every spatial frequency fo is created. In cases where the intensity P corresponding to the spatial frequency fo is present at an end of the histogram, the intensity P corresponding to the spatial frequency fo is substituted by the mean value $\overline{P}$ or the median value of the intensities P of the corresponding spatial frequency components.

The image processing method in accordance with the present invention is not limited to the embodiments wherein Fourier transformation is carried out.

In a still further embodiment of the image processing method in accordance with the present invention, spatial-domain filtering processing is carried out on an image signal such that spatial frequency components corresponding to the striped pattern of the grid image are reduced or eliminated.

Figure 10:
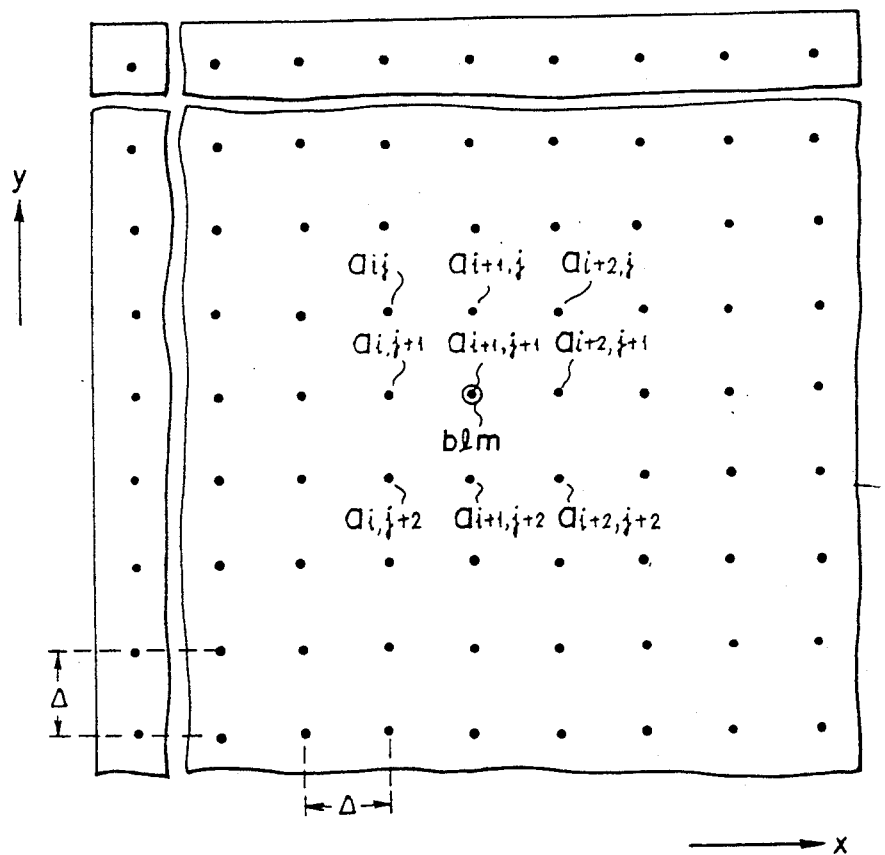
FIG. 10 is an explanatory view showing sampling points located on a stimulable phosphor sheet in order to explain how an example of filtering processing is carried out.

FIG. 10 is an explanatory view showing sampling points located on the stimulable phosphor sheet 11 in order to explain how an example of filtering processing is carried out. In FIG. 10, dots represent the sampling points. The sampling intervals of $\Delta$ are 0.1 mm. The sampling intervals along the x direction (main scanning direction) is set by, for example, adjusting the sampling time intervals in the A/D converter 128 shown in FIG. 7. The sampling intervals along the y direction (sub-scanning direction) is set by, for example, adjusting the speed at which the stimulable phosphor sheet 11 is moved by the sheet conveyance means 15 shown in FIG. 7. Because the sampling intervals of $\Delta$ is set to $\Delta = 0.1$ mm, the image signal obtained in this manner accurately represents the information up to a spatial frequency of 5 cycles/mm and includes the information about the striped pattern having a spatial frequency of 4 cycles/mm. The spatial frequency of 4 cycles/mm of the striped pattern is higher than the spatial frequency of 2.5 cycles/mm, which is the maximum of the desired spatial frequency range necessary for the reproduction of a visible image. For example, in cases where signal compression processing is carried out on the image signal in order to keep the memory capacity required to store the image signal small, as described above with reference to FIGS. 8 and 9A, aliasing corresponding to the striped pattern having a spatial frequency of 4 cycles/mm will occur in the low frequency region. Therefore, even though the spatial frequency of the striped pattern is higher than the spatial frequency of 2.5 cycles/mm, which is the maximum of the desired spatial frequency range necessary for the reproduction of a visible image, it is necessary for the image signal components representing the striped pattern to be eliminated.

Therefore, in this embodiment, filtering processing is carried out in the manner described below.

In FIG. 10, aij, ai+1,j, ... (i,j=1, 2, ...) denote values of the image signal components corresponding to respective sampling points before filtering processing is carried out thereon. Also, blm (l,m=1, 2, ...) denote values of the image signal components obtained from the filtering processing. From the values aij, ai+1,j, ... (i,j=1, 2, ...), values blm (l,m=1, 2, ...) are calculated from the formula expressed as $$blm = \frac{1}{1600} \times (121 \cdot a_{ij} + 198 \cdot a_{i+1,j} + \quad (1)$$
$$121 \cdot a_{i+2,j} + 198 \cdot a_{i,j+1} + 324 \cdot a_{i+1,j+1} + 198 \cdot a_{i+2,j} +$$
$$121 \cdot a_{i,j+2} + 198 \cdot a_{i+1,j+2} + 121 \cdot a_{i+2,j+2})$$

The calculation from Formula (1) is carried out for every sampling point. In this manner, the filtering processing is carried out.

Figure 11:
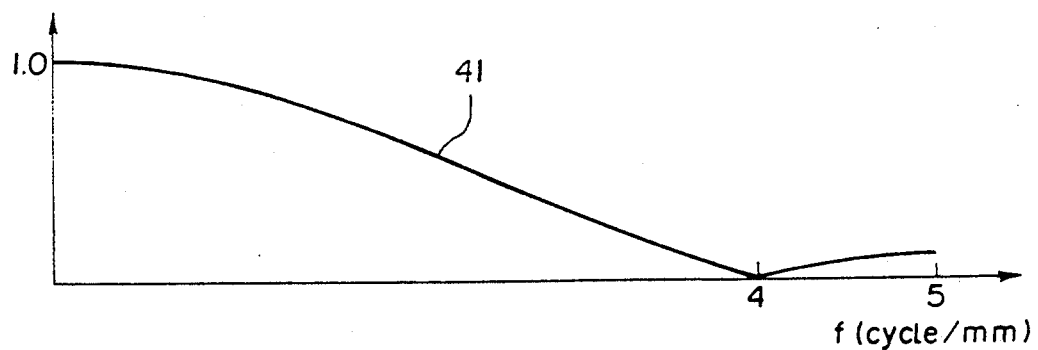
FIG. 11 is a graph showing an example of filter characteristics.

FIG. 11 shows the filtering characteristics of Formula (1).

With reference to FIG. 11, curve 41 represents the filtering characteristics of Formula (1). As illustrated, the transfer characteristics for a spatial frequency of 4 cycles/mm are zero. Therefore, when Formula (1) is used to carry out the filtering processing, an image signal including no information about the striped pattern can be obtained. Accordingly, no noise due to the striped pattern of the grid occurs when signal compression processing, or the like, is carried out on the image signal obtained from the filtering processing. The formula used in the filtering processing is not limited to Formula (1), and may be selected from various formulas in accordance with the spatial frequency of a striped pattern, the spatial frequency range necessary for the reproduction of a visible image, or the like.

As another method for the filtering, the median filtering may be carried out. With the median filtering, in cases where a specific peak is present in the values of image signal components, the peak value is substituted by the median value of the values of the neighboring image signal components which are present in a predetermined region around the image signal component having the peak value. When the image signal components representing the striped pattern are detected as having such a peak value and the medial filtering is carried out appropriately such that these image signal components can be removed, it is possible to eliminate or reduce the adverse effects of the striped pattern due to the grid.

In the aforesaid embodiments of the image processing method in accordance with the present invention, in cases where the direction along which the grid bars extend (i.e. the direction along which the striped pattern extends on the radiation image) is unknown, the filtering processing may be carried out on the image signal components corresponding to positions located along two directions. In cases where the direction along which the striped pattern extends on the radiation image is already known, the filtering processing should preferably be carried out on the image signal components corresponding to positions located along a single direction, i.e. along the direction intersecting perpendicularly to the striped pattern. This is because the time required for the filtering processing to be carried out can be kept short.

Alternatively, in cases where the direction along which the striped pattern extends on the radiation image is unknown, the direction may be detected in the manner described below. Specifically, Fourier transformation is carried out on the image signal components corresponding to positions located along a single line or several lines extending in the main scanning direction (which is indicated by the arrow X in FIG. 7). Also, Fourier transformation is carried out on the image signal components corresponding to positions located along a single line or several lines extending in the sub-scanning direction (which is indicated by the arrow Y in FIG. 7). Peak values among the values of the image signal components are then found, and the direction along which the striped pattern extends is detected from how the positions corresponding to the image signal components having the peak values are located. Thereafter, the adverse effects of the striped pattern can be eliminated by carrying out the filtering processing on the image signal components corresponding to positions located along a single direction.

In cases where the spatial frequency of the striped pattern is unknown, it can be detected in the manner described below. Specifically, Fourier transformation is carried out o the image signal components corresponding to positions located along a single line or several lines extending in the direction that intersects the striped pattern. Thereafter, a spatial frequency corresponding to a peak is found. The spatial frequency of the striped pattern can be determined from the spatial frequency corresponding to the peak. Accordingly, a filtering process having appropriate filtering characteristics can be selected.

Reverting to FIG. 7, the image processing apparatus 150 reduces or eliminates the information representing the noise due to the grid from the image signal by utilizing one of the processes described above. Also, the image processing apparatus 150 carries out other types of image processing on the image signal. The processed image signal is stored and is then fed into an image reproducing apparatus (not shown) which reproduces a visible image from the image signal.

The image processing method in accordance with the present invention is not limited to the aforesaid embodiments. Various other type of filtering processing in the frequency space and the real space can be utilized to reduce or eliminate the adverse effects of the striped pattern corresponding to the grid.

Embodiments of the second method for generating a radiation image signal in accordance with the present invention and embodiments of the radiation image readout apparatus in accordance with the present invention, wherein the second method for generating a radiation image signal is employed, will be described hereinbelow.

FIG. 12 schematically shows a radiation image which has been stored on the stimulable phosphor sheet 11 during the image recording operation using the grid 4. The radiation image comprises an object image 5 (indicated by the oblique lines) and a striped grid image 6

(indicated by vertical stripes) which corresponds to the grid 4 and which is superposed upon the object image 5.

Figure 13:
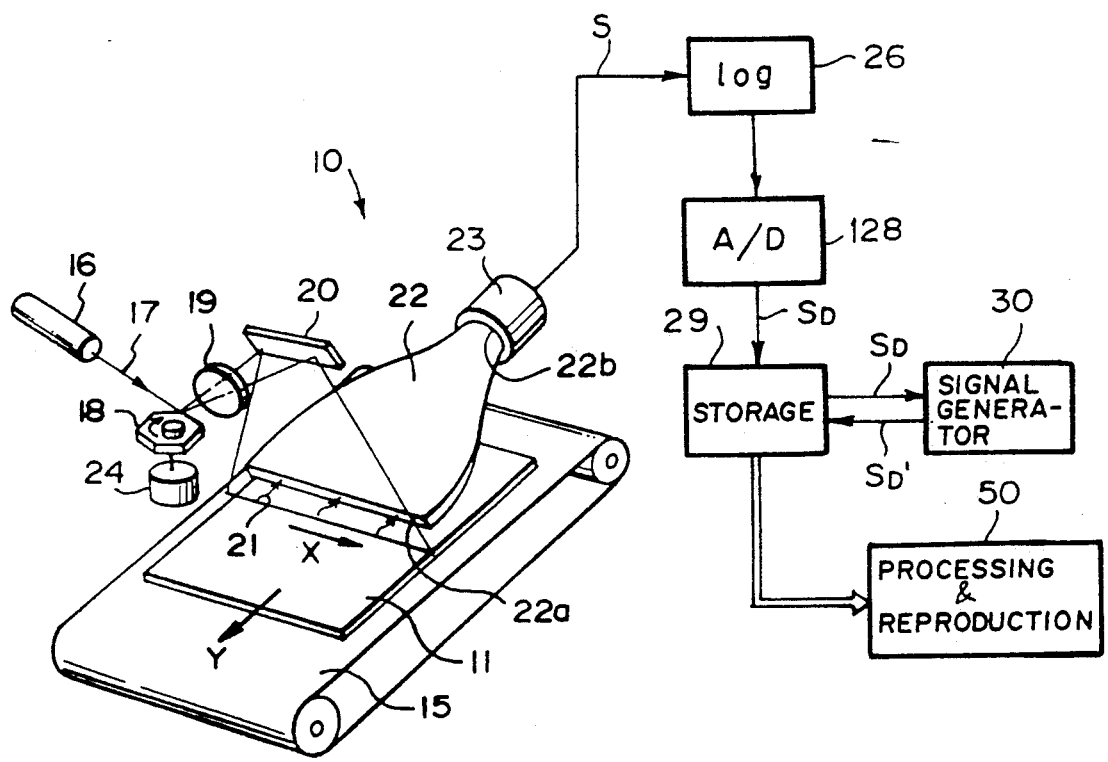
FIG. 13 is a perspective view showing an example of a radiation image read-out apparatus wherein an embodiment of the second method for generating a radiation image signal in accordance with the present invention is employed.

FIG. 13 is a perspective view showing an embodiment of the radiation image read-out apparatus in accordance with the present invention, wherein an embodiment of the second method for generating a radiation image signal in accordance with the present invention is employed. In FIG. 13, similar elements are numbered with the same reference numerals with respect to FIG. 3. The reference numeral 10 denotes a read-out means.

With reference to FIG. 13, the radiation image is read out from the stimulable phosphor sheet 11 shown in FIG. 12 in the same manner as described above, and an analog output signal S is generated by the photomultiplier 23. The analog output signal S includes signal components falling in the spatial frequency region above the spatial frequency fss=2.5 (cycles/mm), which is the maximum of a desired spatial frequency range necessary for the reproduction of a visible radiation image having good image quality. Particularly, the analog output signal S includes the signal components, which represents the grid image 6 shown in FIG. 12 and which fall in the spatial frequency region above the spatial frequency fss. The signal components representing the grid image 6 adversely affect the image quality of a reproduced visible image and must be reduced or eliminated.

The analog output signal S is logarithmically amplified by the logarithmic amplifier 26. In an A/D converter 128, the amplified analog output signal S is sampled at predetermined sampling intervals, and the sampled image signal is digitized into a digital image signal SD (original image signal). The original image signal SD is stored in the storage means 29.

Figure 14:
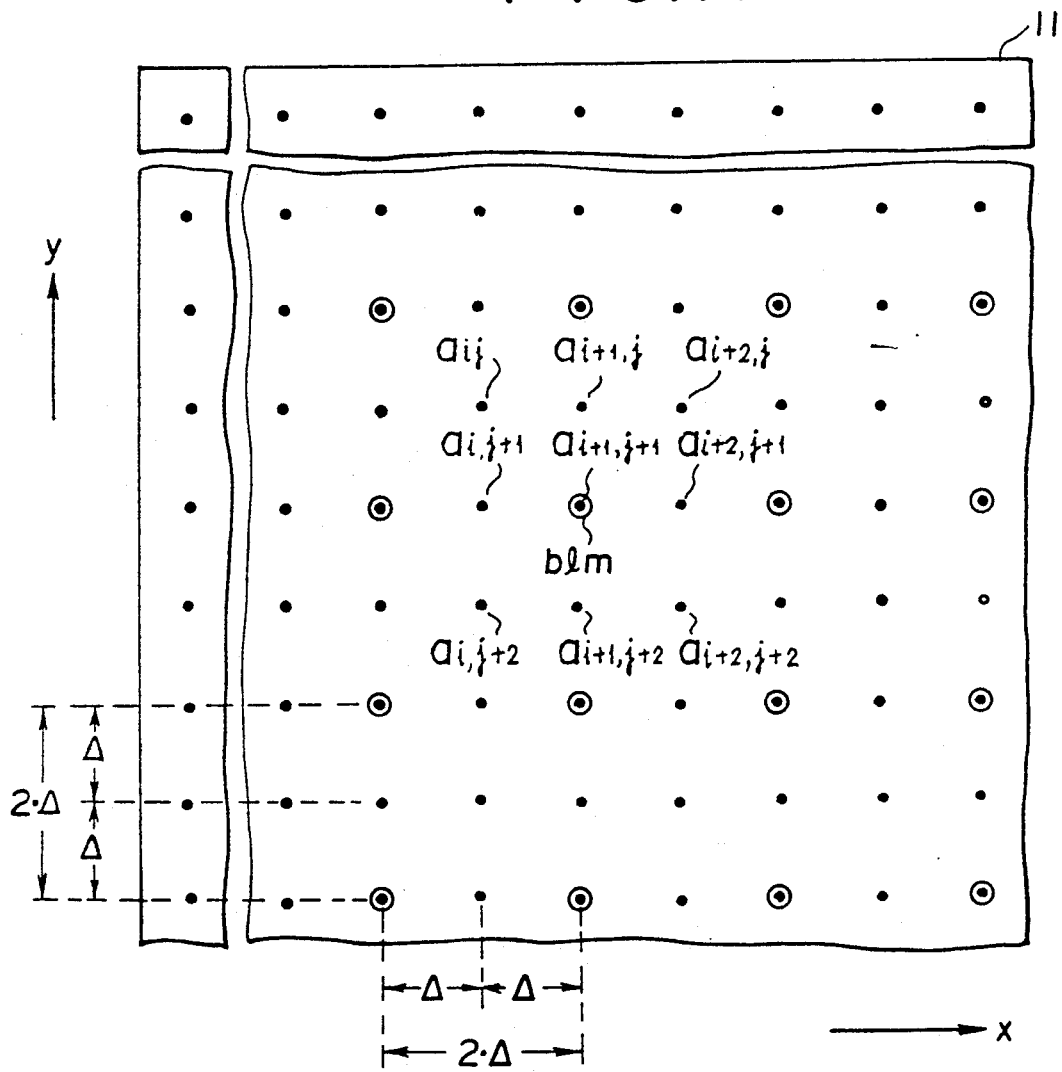
FIG. 14 is an explanatory view showing sampling points located on a stimulable phosphor sheet in order to explain how an example of filtering processing is carried out.

FIG. 14 shows sampling points located on the stimulable phosphor sheet 11. In FIG. 14, the horizontal direction (x direction) corresponds to the main scanning direction indicated by the arrow X in FIG. 13 and the vertical direction (y direction) corresponds to the subscanning direction indicated by the arrow Y in FIG. 13. Dots represent the sampling points from which the original image signal SD is sampled. Circles represent the sampling points at which an image signal is resampled from the original image signal SD. In this embodiment, in the course of obtaining the original image signal SD, the amplified analog output signal S is sampled at sampling intervals of $\Delta = 1/(2 \cdot fsw) = 0.1(mm)$ corresponding to a spatial frequency fsw=5.0 (cycles/mm) along both the x direction (main scanning direction) and the y direction (subscanning direction). The spatial frequency fsw is two times as high as the spatial frequency fss=2.5 (cycles/mm), which is the maximum of the desired spatial frequency range necessary for the readout of the radiation image recorded on the stimulable phosphor sheet 11. The sampling intervals of $\Delta=0.1$ (mm) are one-half of the sampling intervals of $2 \cdot \Delta = 1/(2 \cdot fss) = 0.2(mm)$ corresponding to the spatial frequency fss=2.5 (cycles/mm). By way of example, the sampling intervals along the x direction (main scanning direction) can be set by adjusting the sampling time intervals in the A/D converter 128 shown in FIG. 13. The sampling intervals along the y direction (sub-scanning direction) can be set by, for example, adjusting the speed at which the stimulable phosphor sheet 11 is moved by the sheet conveyance means 15 shown in FIG. 13.

The original image signal SD sampled from the amplified analog output signal S at the sampling intervals (0.1 mm) indicated by the dots in FIG. 14 includes the information below fsw=5.0 (cycles/mm). Therefore, the original image signal SD also includes the information (4.0 cycles/mm) representing the striped pattern of the grid image 6 shown in FIG. 12. In this embodiment, aliasing of the striped pattern of the grid image 6 does not occur.

The original image signal SD is stored in the storage means 29 shown in FIG. 13, and is fed therefrom into an image signal generating means 30. The image signal generating means 30 carries out filtering processing and resampling processing in the manner described below. The resampling processing is carried out such that an image signal is sampled at sampling intervals of $2 \cdot \Delta = 1/(2 \cdot fss) = 0.2(mm)$, which correspond to the spatial frequency fss=2.5 (cycles/mm). Therefore, the image signal generating means 30 serves both as the filtering means and as the sampling means.

In FIG. 14, aij, ai+1,j, ... (i,j=1, 2, ...) denote values of the original image signal SD corresponding to respective sampling points. From the values aij, ai+1,j, ... (i,j=1, 2, ...), values blm (l,m=1, 2, ...) of a resampled image signal SD' are calculated from the formula expressed as $$blm = \frac{1}{1600} \times (121 \cdot a_{ij} + 198 \cdot a_{i+1,j} + \quad (2)$$

$$121 \cdot a_{i+2,j} + 198 \cdot a_{i,j+1} + 324 \cdot a_{i+1,j+1} + 198 \cdot a_{i+2,j} +$$

$$121 \cdot a_{i,j+2} + 198 \cdot a_{i+1,j+2} + 121 \cdot a_{i+2,j+2})$$

The calculation from Formula (2) is carried out for the original image signal SD representing the image information stored over the whole surface of the stimulable phosphor sheet 11. In this manner, the filtering processing and the resampling processing (wherein the number of the sampling points is reduced to one-half in both the x and y directions) are carried out simultaneously.

The filtering characteristics of Formula (2) are shown in FIG. 11.

With reference to FIG. 11, curve 41 represents the filtering characteristics of Formula (2). As illustrated, the transfer characteristics for a spatial frequency of 4 cycles/mm are zero. Therefore, when Formula (2) is used in obtaining the image signal SD', the image signal SD' including no information about the striped pattern of the grid image 6 can be obtained. Also, as illustrated in FIG. 14, the image signal SD' is sampled at sampling intervals of $2 \cdot \Delta = 0.2(mm)$. Therefore, the image signal SD' includes the information below the spatial frequency fss=2.5 (cycles/mm), which information is necessary for the reproduction of a visible image, and does not include the information representing the striped pattern due to the grid 4. Accordingly, a visible image having good image quality can be reproduced from the image signal SD'

Figure 15:
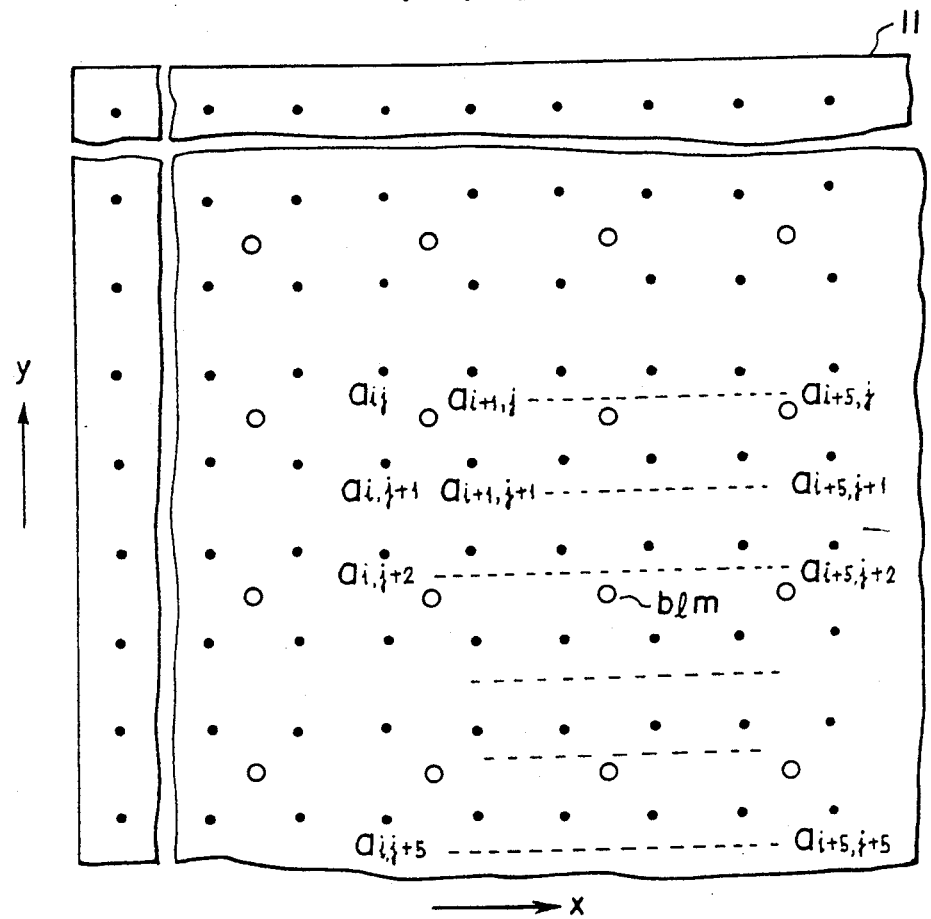
FIG. 15 is an explanatory view showing sampling points located on a stimulable phosphor sheet in order t explain how another example of filtering processing is carried out.

FIG. 15 shows sampling points located on the stimulable phosphor sheet 11 in order to explain how another example of filtering processing is carried out. In FIG. 15, dots represent the sampling points from which the original image signal SD is sampled. Circles represent the sampling points at which an image signal is resampled from the original image signal SD.

In the embodiment of FIG. 15, from values aij, ai+1,j, ... (i,j=1, 2, ...) of the original image signal SD corresponding to the respective sampling points, values blm (l,m=1, 2, ...) of the image signal after being resampled are calculated from the formula expressed as $$blm = \frac{1}{324} \times (a_{i,j} - 2 \cdot a_{i+1,j} - 8 \cdot a_{i+2,j} - \quad (3)$$

$8 \cdot a_{i+3,j} - 2 \cdot a_{i+4,j} + a_{i+5,j} - 2 \cdot a_{i,j+1} + 4 \cdot a_{i+1,j+1} +$
$16 \cdot a_{i+2,j+1} + 16 \cdot a_{i+3,j+1} + 4 \cdot a_{i+4,j+1} - 2 \cdot a_{i+5,j+1} -$
$8 \cdot a_{i,j+2} + 16 \cdot a_{i+1,j+2} + 64 \cdot a_{i+2,j+2} + 64 \cdot a_{i+3,j+2}) +$
$16 \cdot a_{i+4,j+2} - 8 \cdot a_{i+5,j+2} - 8 \cdot a_{i,j+3} + 16 \cdot a_{i+1,j+3} +$
$64 \cdot a_{i+2,j+3} + 64 \cdot a_{i+3,j+3} + 16 \cdot a_{i+4,j+3} - 8 \cdot a_{i+5,j+3} -$
$2 \cdot a_{i,j+4} + 4 \cdot a_{i+1,j+4} + 16 \cdot a_{i+2,j+4} + 16 \cdot a_{i+3,j+4} +$
$4 \cdot a_{i+4,j+4} - 2 \cdot a_{i+5,j+4} + a_{i,j+5} - 2 \cdot a_{i+1,j+5} - 8 \cdot a_{i+2,j+5} -$ $8 \cdot a_{i+3,j+5} - 2 \cdot a_{i+4,j+5} + a_{i+5,j+5}$ The calculation from Formula (3) is carried out on the original image signal SD representing the image information stored over the whole surface of the stimulable phosphor sheet 11. In this manner, the filtering processing and the resampling processing are carried out simultaneously.

Figure 16:
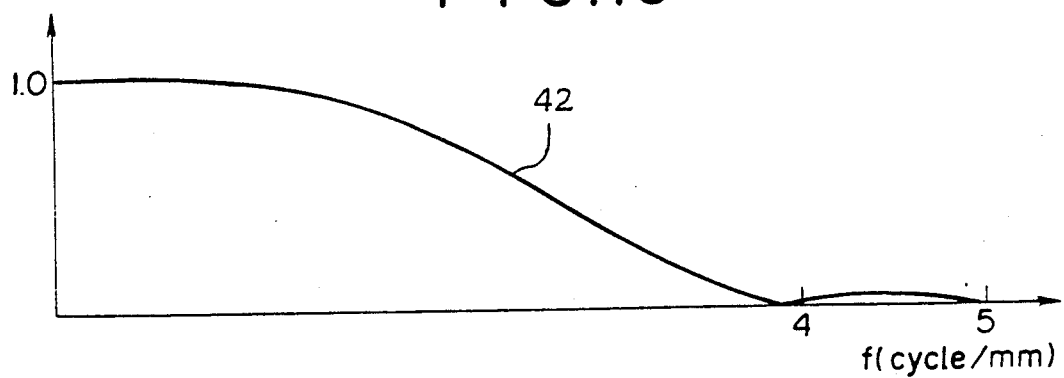
FIG. 16 is a graph showing another example of filter characteristics.

FIG. 16 shows the filtering characteristics of Formula (3).

With reference to FIG. 16, curve 42 represents the filtering characteristics of Formula (3). As illustrated, the transfer characteristics for a spatial frequency range of 4 to 5 cycles/mm are nearly zero. Therefore, when Formula (3) is used in obtaining the image signal SD' at sampling intervals of $2 \cdot = 0.2(mm)$, the adverse effects of the striped pattern due to the grid 4 are removed.

In the manner described above, the image signal generating means 30 shown in FIG. 13 generates the image signal SD', which includes little or no adverse effects of the striped pattern of the grid 4 and which has been resampled at sampling intervals corresponding to the spatial frequency fss which is the maximum of the desired spatial frequency range necessary for the reproduction of a visible image. The image signal SD' is stored in the storage means 29 and is then fed therefrom into the image processing and reproducing apparatus 50. The image processing and reproducing apparatus 50 carries out the appropriate image processing on the image signal SD' and reproduces a visible image from the processed image signal SD'. Because the image signal SD' fed into the image processing and reproducing apparatus 50 includes little or no adverse effects of the grid 4, a visible image having good image quality can be reproduced from the image signal SD'.

In the aforesaid embodiments of the second method for generating a radiation image signal in accordance with the present invention, the spatial frequency fsw=5.0 (cycles/mm) two times as high as the spatial frequency fss=2.5 (cycles/mm) (a spatial frequency fsw which is integral multiples of the spatial frequency fss) is selected as the spatial frequency fsw corresponding to sampling intervals of Δ at which the original image signal SD is obtained. Also, the filtering processing and the resampling processing are carried out simultaneously. However, the spatial frequency fsw need not necessarily be integral multiples of the spatial frequency fss. Also, the filtering processing and the resampling processing need not necessarily be carried out simultaneously.

Figure 17:
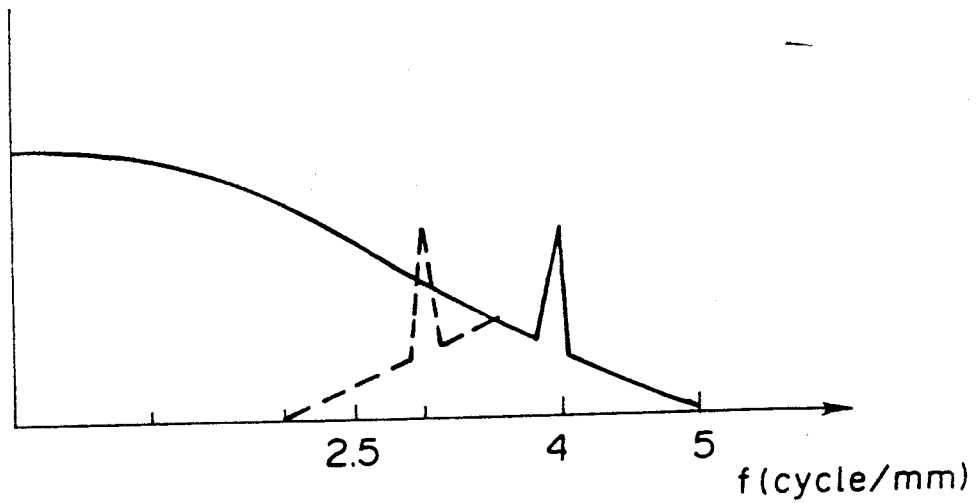
FIG. 17 is a graph showing the spatial frequency characteristics of a radiation image, which has been stored on a stimulable phosphor sheet and which comprises an object image and a grid image superposed upon the object image, along a direction intersecting perpendicularly to the striped pattern of the grid image, and aliasing which occurs in an original image signal sampled at sampling intervals of $\Delta = 1/(2 \times 3.5) = 0.14$ (mm) corresponding to a spatial frequency of 3.5 cycles/mm.

FIG. 17 is an explanatory graph showing how aliasing occurs when a spatial frequency of 3.5 cycles/mm is employed as the Nyquist spatial frequency fsw corresponding to sampling intervals of Δ at which the original image signal SD is obtained. In FIG. 17, the solid line indicates the spatial frequency characteristics of the radiation image, which has been stored on the stimulable phosphor sheet 11, along a direction intersecting perpendicularly to the striped pattern of the grid image 6 shown in FIG. 12. The broken line indicates how aliasing occurs.

As described above, in this case, a spatial frequency of 3.5 cycles/mm is employed as the spatial frequency fsw corresponding to sampling intervals of Δ at which the original image signal SD is obtained. Therefore, aliasing due to the striped pattern at a spatial frequency of 4 cycles/mm occurs at the position corresponding to a spatial frequency of 3 cycles/mm.

In such a case, filtering processing is carried out on the original image signal SD such that the frequency components of 3 cycles/mm are attenuated or eliminated. Also, the resampling is carried out at sampling intervals corresponding to fss=2.5 (cycles/mm).

In the aforesaid embodiments of the second method for generating a radiation image signal in accordance with the present invention, filtering processing is carried out on the image signal components corresponding to positions located along two directions. This is because it is assumed that the direction along which the grid bars extends during the recording of the radiation image is unknown or not constant, or that the direction along which the striped pattern extends on the stimulable phosphor sheet 11 during the readout of the radiation image is unknown or not constant. In cases where the direction along which the striped pattern extends on the stimulable phosphor sheet 11 is constant and coincides with, for example, the main scanning direction (indicated by the arrow X in FIG. 13), or when the direction can be detected, the filtering processing may be carried out only on the image signal components corresponding to positions located along the direction intersecting perpendicularly to the striped pattern. Alternatively, also when the direction along which the striped pattern extends on the stimulable phosphor sheet 11 is already known, the filtering processing may be carried out on the image signal components corresponding to positions located along two directions.

During the recording of radiation images, several types of grids different in their bar pitches (at which the lead bars 4a, 4a, ... and the aluminium bars 4b, 4b, ... shown in FIG. 1 are located alternately) may be used. Processing in such cases will be described hereinbelow.

By way of example, four types of grids having pitches of 3.3, 4.0, 4.3, and 6.0 cycles/mm are prepared. During the recording of a radiation image, one of these grids is used in accordance with the purpose for which the radiation image is used. In the example described below, the grid having pitches of 4.0 cycles/mm is used.

Figure 18:
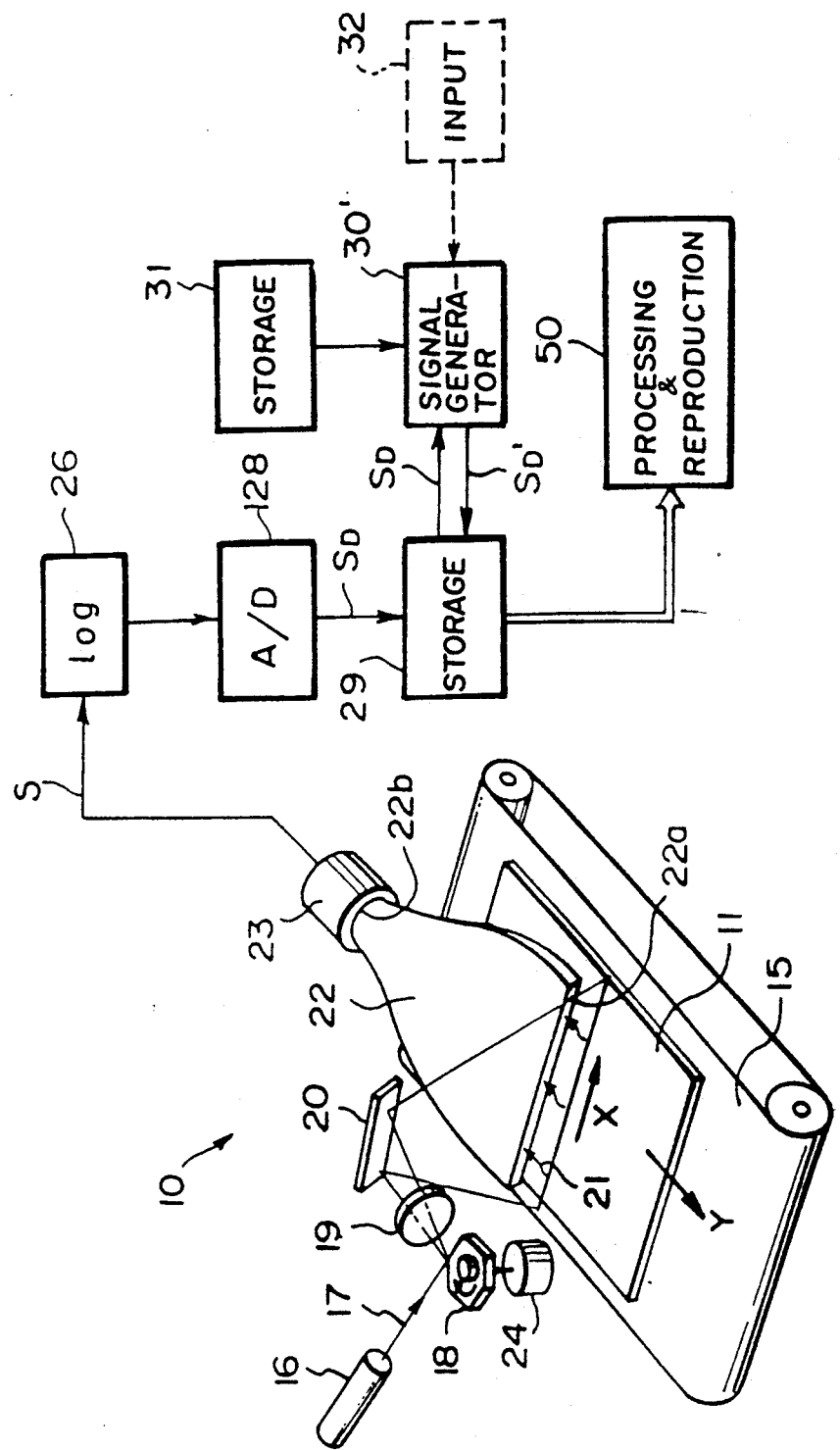
FIG. 18 is a perspective view showing an embodiment of the radiation image read-out apparatus in accordance with the present invention, which is applicable when several types of grids are used during the recording of radiation images.

FIG. 18 is a perspective view showing an embodiment of the radiation image read-out apparatus in accordance with the present invention, which is applicable when several types of grids are used during the recording of radiation images. In FIG. 18, similar elements are numbered with the same reference numerals with respect to FIG. 13.

In the same manner as in the embodiment of FIG. 13, the original image signal SD representing the radiation image is obtained and stored in the storage means 29. As described with reference to FIG. 14, the original image signal SD is obtained from the sampling at sampling intervals of $\Delta = 1/(2 \cdot fsw) = 0.1 (mm)$ corresponding to a spatial frequency fsw=5.0 (cycles/mm) two times as high as the spatial frequency fss=2.5 (cycles/mm), which is the maximum of the desired spatial frequency range necessary for the readout of the radiation image recorded on the stimulable phosphor sheet 11. Therefore, when the grid having pitches of 3.3 cycles/mm was used during the recording of a radiation image and the original image signal SD is obtained from the radiation image, the spatial frequency of the information, which represents the striped pattern due to the grid and which is included in the original image signal SD, is 3.3 cycles/mm. Also, when the grids having pitches of 4.0 and 4.3 cycles/mm, respectively, were used during the recording of radiation images and the original image signals SD are obtained from the radiation images, the spatial frequencies of the information, which represents the striped patterns due to the grids and which is included in the original image signals SD, are 4.0 and 4.3 cycles/mm. In cases where the grid having pitches of 6.0 cycles/mm was used during the recording of a radiation image, aliasing occurs at a frequency of 4.0 cycles/mm, and the spatial frequency of the information, which represents the striped pattern and which is included in the original image signal SD, is 4.0 cycles/mm as in the case where the grid having pitches of 4.0 cycles/mm was used.

The original image signal SD is stored in the storage means 29 and is then fed into an image signal generating means 30'. Like the image signal generating means 30 shown in FIG. 13, the image signal generating means 30' serves both as the filtering means and as the sampling means. The image signal generating means 30' also serves as a judgment means. Specifically, from the original image signal SD, the image signal generating means 30' determines the spatial frequency of the grid image recorded together with the object image or the spatial frequency of the aliasing caused to occur by the grid image.

For this purpose, the image signal generating means 30' carries out Fourier transformation on the image signal components of the original image signal SD corresponding to positions located along several scanning lines extending in the x direction shown in FIG. 12. Also, the image signal generating means 30' carries out Fourier transformation on the image signal components of the original image signal SD corresponding to positions located along several scanning lines extending in the y direction shown in FIG. 12.

Figure 19A:
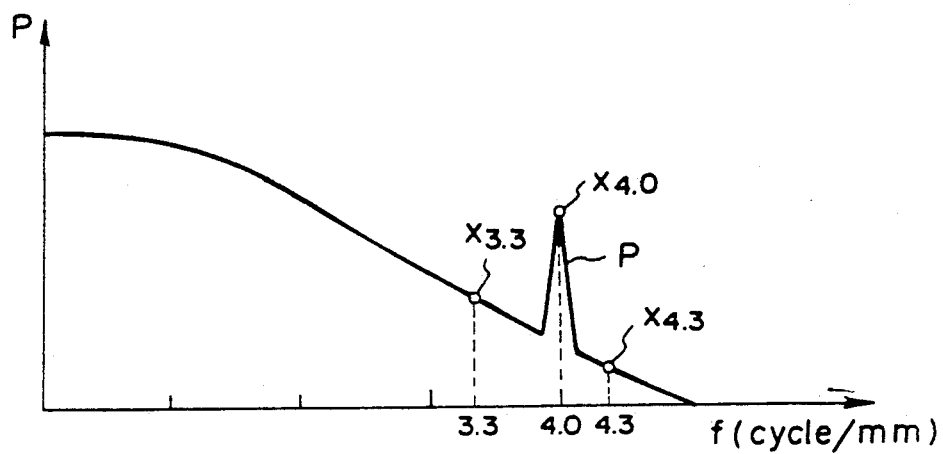
FIG. 19A is a graph showing a spatial frequency distribution of a signal along the x direction, which signal is obtained from Fourier transformation carried out on an original image signal.
Figure 19B:
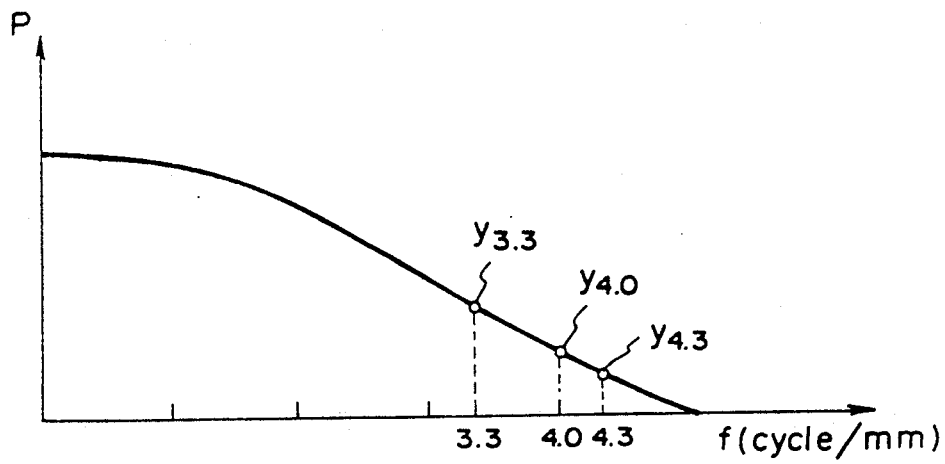
FIG. 19B is a graph showing a spatial frequency distribution of a signal along the y direction, which signal is obtained from Fourier transformation carried out on an original image signal.

FIG. 19A is a graph showing a spatial frequency distribution of a signal along the x direction, which signal is obtained from Fourier transformation carried out on the original image signal SD. FIG. 19B is a graph showing a spatial frequency distribution of a signal along the y direction, which signal is obtained from Fourier transformation carried out on the original image signal SD.

In this embodiment, the grid having pitches of 4.0 cycles/mm was positioned such that the striped pattern of the grid image 6 shown in FIG. 12 extends along the y direction and the stripes of the striped pattern stand side by side along the x direction. Therefore, as illustrated in FIG. 19A, a peak P occurs at the position corresponding to a spatial frequency of 4.0 cycles/mm. In FIG. 19A, x3.3, x4.0, and x4.3 respectively denote the values of the components having spatial frequencies of 3.3, 4.0, and 4.3 cycles/mm with respect to the x direction. Also, in FIG. 19B, y3.3, y4.0, and y4.3 respectively denote the values of the components having spatial frequencies of 3.3, 4.0, and 4.3 cycles/mm with respect to the y direction. The mean value M of the values of these components is calculated from the formula expressed as $$M = \frac{x_{3.3} + x_{4.0} + x_{4.3} + y_{3.3} + y_{4.0} + y_{4.3}}{6} \quad (4)$$

The values x3.3, x4.0, x4.3, y3.3, y4.0, and y4.3 are compared with the product A*M of the mean value M and a factor A (for example, 4.0). In cases where a value exceeding A*M is present, it is judged that a grid was used during the recording of the radiation image and that the adverse effects of the grid occur at the spatial frequency corresponding to said value. Specifically, in this embodiment, the conditions $$x_{4.0} > A \cdot M \ldots \quad (5)$$

and $$x_{3.3}, x_{4.3}, y_{3.3}, y_{4.3} > A \cdot M \ldots \quad (6)$$

are satisfied. Therefore, it is judged that a striped pattern occurs at pitches of 4.0 cycles/mm along the x direction due to the adverse effects of the grid. The striped pattern at pitches of 4.0 cycles/mm occurs when the grid having pitches of 4.0 cycles/mm was used and when the grid having pitches of 6.0 cycles/mm was used. However, it is not necessary to judge which one of these grids was used during the recording of the radiation image.

A second storage means 31 shown in FIG. 18 stores information representing three filtering processing methods which are to be used respectively in order to eliminate the peaks occurring at spatial frequencies of 3.3, 4.0, and 4.3 cycles/mm with respect to the x direction. The second storage means 31 also stores information representing three filtering processing methods which are to be used respectively in order to eliminate the peaks occurring at spatial frequencies of 3.3, 4.0, and 4.3 cycles/mm with respect to the y direction.

After judging that the peak is present at a spatial frequency of 4.0 cycles/mm with respect to the x direction, the image signal generating means 30' reads the information, which represents the filtering processing method suitable for eliminating the peak, from the second storage means 31. Thereafter, the image signal generating means 30' carries out the filtering processing and the sampling processing in order to obtain an image signal SD'. The image signal SD' includes the information below the spatial frequency fss=2.5 (cycles/mm), which information is necessary for the reproduction of a visible image, and does not include the information representing the striped pattern due to the grid. Accordingly, a visible image having good image quality can be reproduced from the image signal SD'.

In this embodiment, judgment is made as to whether a peak is found along the x direction or along the y direction. In cases where grids are always located along the same direction during the recording of radiation images, the presence or absence of a peak and its position may be detected only with respect to the direction intersecting the striped pattern. Also, in the aforesaid embodiment, the image signal generating means 30' judges the presence or absence of a peak and its position from the original image signal SD. Alternatively, as shown in FIG. 18, an input means 32 comprising a keyboard, or the like, may be provided and used to enter information about the type of the grid, which is used during the recording of a radiation image, manually.

In the aforesaid embodiments of the second method for generating a radiation image signal in accordance with the present invention and the radiation image read-out apparatus wherein the second method is employed, stimulable phosphor sheets are used. However, the second method for generating a radiation image signal and the radiation image read-out apparatus in accordance with the present invention are widely applicable when radiation image signals are obtained from radiation images, which have been recorded on recording media during image recording operations using grids and each of which comprises an object image and a striped grid image corresponding to the grid and superposed upon the object image. For example, the second method for generating a radiation image signal and the radiation image read-out apparatus in accordance with the present invention are applicable also when X-ray image signals are detected from X-ray films having X-ray images recorded thereon.

We claim:

1. A method for generating a radiation image signal, which comprises the steps of:
   i) detecting an image signal by reading out a radiation image which has been recorded on a recording medium during an image recording operation using a grid and which comprises an object image and a striped grid image corresponding to the grid and superposed upon the object image, and
   ii) sampling said image signal such that a plurality of image signal components are obtained which correspond to a plurality of discrete points on said radiation image, intervals between said discrete points varying irregularly from predetermined intervals at least along a direction intersecting the striped pattern of said grid image on said radiation image.

2. A method for generating a radiation image signal as defined in claim 1 wherein said recording medium is a stimulable phosphor sheet on which a radiation image has been stored.

3. A method for generating a radiation image signal as defined in claim 2 wherein said image signal is detected from a read-out operation wherein said stimulable phosphor sheet is exposed to stimulating rays which cause said stimulable phosphor sheet to emit light in proportion to the amount of energy stored thereon during exposure to radiation, and the emitted light is detected photoelectrically.

4. A method for generating a radiation image signal as defined in claim 3 wherein said stimulating rays are a laser beam.

5. A method for generating a radiation image signal as defined in claim 1 wherein said recording medium is photographic film.

6. An image processing method for processing a radiation image signal, which comprises the steps of:
   i) carrying out a Fourier transformation on said radiation image signal detected by reading out a radiation image which has been recorded on a recording medium during a radiation image recording operation using a grid, said radiation image comprising an object image and a striped grid image corresponding to the grid, said striped grid image being superposed upon the object image,
   ii) reducing or eliminating frequency information, corresponding to the striped grid image from frequency information, corresponding to the radiation image, said radiation image frequency information being obtained from the Fourier transformation, and
   iii) carrying out an inverse Fourier transformation on frequency information obtained from the reducing or eliminating step.

7. An image processing method as defined in claim 6 wherein said recording medium is a stimulable phosphor sheet on which said radiation image has been stored.

8. An image processing method as defined in claim 7 wherein said image signal is detected from a read-out operation wherein said stimulable phosphor sheet is exposed to stimulating rays which cause said stimulable phosphor sheet to emit light in proportion to an amount of energy stored thereon during exposure to radiation, said emitted light being detected photoelectrically.

9. An image processing method as defined in claim 8 wherein said stimulating rays are a laser beam.

10. An image processing method as defined in claim 6 wherein said recording medium is photographic film.

11. An image processing method for processing a radiation image signal, which comprises the steps of:
    i) carrying out spatial-domain filtering processing on a radiation image signal detected by reading out a radiation image which has been recorded on a recording medium during a radiation image recording operation using a grid, said radiation image comprising an object image and a striped grid image corresponding to the grid, said striped grid image being superposed upon the object image,
    ii) effecting said spatial-domain filtering processing such that spatial frequency components corresponding to the striped grid image are reduced or eliminated.

12. An image processing method as defined in claim 11 wherein said recording medium is a stimulable phosphor sheet on which radiation image has been stored.

13. An image processing method as defined in claim 12 wherein said image signal is detected from a read-out operation wherein said stimulable phosphor sheet is exposed to stimulating rays which cause said stimulable phosphor sheet to emit light in proportion to an amount of energy stored thereon during exposure to radiation, said emitted light being detected photoelectrically.

14. An image processing method as defined in claim 13 wherein said stimulating rays are a laser beam.

15. An image processing method as defined in claim 11 wherein said recording medium is photographic film.

16. A method for generating a radiation image signal, wherein an image signal is detected by reading out a radiation image at predetermined sampling intervals from a recording medium on which the radiation image has been recorded during an image recording operation using a grid, said radiation image comprising an object image and a striped grid image corresponding to the grid, said striped grid image being superposed upon the object image and having spatial frequencies higher than a spatial frequency, which is the maximum of a desired spatial frequency range,
    the method for generating a radiation image signal comprising the steps of:
    i) sampling an original image signal, while reading out said radiation image, by applying sampling intervals smaller than sampling intervals which corresponds to an aliasing spatial frequency caused by said grid image, said smaller sampling intervals being applied along at least a direction intersecting a striped pattern of said grid image, ii) subjecting said original image signal to filter processing for reducing or eliminating spatial frequency components corresponding to said striped pattern or to said aliasing, and iii) generating an image signal by sampling the original image signal, which has been obtained from said filter processing, at sampling intervals such that said spatial frequency, which is a maximum of the desired spatial frequency range, is set as a Nyquist frequency.

17. A method for generating a radiation image signal as defined in claim 16 wherein said recording medium is a stimulable phosphor sheet on which a radiation image has been stored.

18. A method for generating a radiation image signal as defined in claim 17 wherein said image signal is detected from a read-out operation wherein said stimulable phosphor sheet is exposed to stimulating rays which cause said stimulable phosphor sheet to emit light in proportion to an amount of energy stored thereon during exposure to radiation, said emitted light being detected photoelectrically.

19. A method for generating a radiation image signal as defined in claim 18 wherein said stimulating rays are a laser beam.

20. A method for generating a radiation image signal as defined in claim 16 wherein said recording medium is photographic film.

21. A radiation image read-out apparatus, wherein an image signal is detected by reading out a radiation image at predetermined sampling intervals from a recording medium on which the radiation image has been recorded during an image recording operation using a grid, said radiation image comprising an object image and a striped grid image corresponding to the grid, said striped grid being superposed upon the object image band having spatial frequencies higher than a spatial frequency, which is the maximum of a desired spatial frequency range, wherein the improvement comprises:

i) a read-out means for reading out said radiation image and for obtaining an original image signal by applying sampling intervals smaller than sampling intervals, which correspond to an aliasing spatial frequency caused by said grid image, wherein said smaller sampling interval coincides with said spatial frequency, which is a maximum of the desired spatial frequency range, along at least a direction intersecting a striped pattern of said grid image, ii) a filtering means, which carries out filter processing on said original image signal, for reducing or eliminating spatial frequency components corresponding to said striped pattern or to said aliasing, and iii) a sampling means for generating an image signal by sampling the original image signal, wherein said original image signal is obtained from said filter processing and said sampling intervals corresponding to said maximum desired spatial frequency range, is set as a Nyquist frequency.

22. A radiation image read-out apparatus as defined in claim 21 further comprising a storage means for storing information about several types of grids, wherein each of said grid types has a recorded image representing different spatial frequencies, and said storage means storing information about several processes for reducing or eliminating spatial frequency components corresponding to said striped pattern or to said aliasing, each of said filtering processes corresponding to a respective grid type, input means for entering information about the type of grid used during recordation of said radiation image, and said filtering means reading information about one of the filtering processes, which corresponds to the type of grid entered by said input means, from said storage means and carrying out filter processing on said original image signal by using said one filtering process read from said storage means.

23. A radiation image read-out apparatus as defined in claim 21 further comprising: storage means for storing information about several types of grids, the recorded images of which have different spatial frequencies, and information about several types of filtering processes for reducing or eliminating spatial frequency components corresponding to said striped pattern or to said aliasing, wherein each of said filtering processes corresponds to a respective grid type, a judgement means for determining, from said original signal, a spatial frequency of the grid image recorded together with said object image or a spatial frequency of the aliasing caused to occur by said grid image, and said filtering means reading the information about the filtering process, which corresponds to the spatial frequency of said grid image or of said aliasing determined by said judgement means, from said storage means and carries out said filtering process on said original image signal by using said filtering process read from said storage means.

24. A radiation image read-out apparatus as defined in claim 21 wherein said recording medium is a stimulable phosphor sheet on which a radiation image has been stored.

25. A radiation image read-out apparatus as defined in claim 24 wherein said image signal is detected from a read-out operation wherein said stimulable phosphor sheet is exposed to stimulating rays which cause said stimulable phosphor sheet to emit light in proportion to an amount of energy stored thereon during exposure to radiation, said emitted light being detected photoelectrically.

26. A radiation image read-out apparatus as defined in claim 25 wherein said stimulating rays are a laser beam.

27. A radiation image read-out apparatus as defined in claim 21 wherein said recording medium is photographic film.

28. A radiation image read-out apparatus as defined in claim 22 wherein said recording medium is a stimulable phosphor sheet on which a radiation image has been stored.

29. A radiation image read-out apparatus as defined in claim 28 wherein said image signal is detected from a read-out operation wherein said stimulable phosphor sheet is exposed to stimulating rays which cause said stimulable phosphor sheet to emit light in proportion to an amount of energy stored thereon during exposure to radiation, said emitted light being detected photoelectrically.

30. A radiation image read-out apparatus as defined in claim 29 wherein said stimulating rays are a laser beam.

31. A radiation image read-out apparatus as defined in claim 22 wherein said recording medium is photographic film.

32. A radiation image read-out apparatus as defined in claim 23 wherein said recording medium is a stimulable phosphor sheet on which a radiation image has been stored.

33. A radiation image read-out apparatus as defined in claim 32 wherein said image signal is detected from a read-out operation wherein said stimulable phosphor sheet is exposed to stimulating rays which cause said stimulable phosphor sheet to emit light in proportion to an amount of energy stored thereon during exposure to radiation, said emitted light being detected photoelectrically.

34. A radiation image read-out apparatus as defined in claim 33 wherein said stimulating rays are a laser beam.

35. A radiation image read-out apparatus as defined in claim 23 wherein said recording medium is photographic film.

* * * * *